(12) United States Patent
Fukuda

(10) Patent No.: US 11,464,471 B2
(45) Date of Patent: Oct. 11, 2022

(54) IMAGE DISPLAY DEVICE, IMAGE DISPLAY METHOD, IMAGE DISPLAY PROGRAM, IMAGE MANAGEMENT DEVICE, IMAGE MANAGEMENT METHOD, AND IMAGE MANAGEMENT PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

(21) Appl. No.: 16/938,033

(22) Filed: Jul. 24, 2020

(65) Prior Publication Data

US 2021/0059622 A1 Mar. 4, 2021

(30) Foreign Application Priority Data

Aug. 27, 2019 (JP) .............................. JP2019-154276

(51) Int. Cl.
*A61B 6/00* (2006.01)

(52) U.S. Cl.
CPC .............. *A61B 6/502* (2013.01); *A61B 6/461* (2013.01); *A61B 6/5217* (2013.01); *A61B 6/5294* (2013.01)

(58) Field of Classification Search
CPC ....... A61B 6/502; A61B 6/461; A61B 6/5217; A61B 6/5294; A61B 6/563; A61B 6/463; A61B 6/025; G16H 40/67; G16H 30/20
See application file for complete search history.

(56) References Cited

U.S. PATENT DOCUMENTS 8,983,156 B2 3/2015 Periaswamy et al.
2003/0179915 A1 9/2003 Goto 2005/0107689 A1* 5/2005 Sasano ................... A61B 6/032
600/425
2006/0098855 A1 5/2006 Gkanatsios et al.
2008/0075341 A1 3/2008 Goto
2009/0123052 A1 5/2009 Ruth et al.
(Continued)

FOREIGN PATENT DOCUMENTS

EP 2 846 284 A2 3/2015
EP 2849106 A2 3/2015
(Continued)

OTHER PUBLICATIONS

The extended European search report issued by the European Patent Office dated Apr. 13, 2021, which corresponds to European Patent Application No. 20191411.6-1126 and is related to U.S. Appl. No. 16/938,033.
(Continued)

*Primary Examiner* — Courtney D Thomas
(74) *Attorney, Agent, or Firm* — Studebaker & Brackett PC

(57) ABSTRACT

A display control unit displays, on a display unit, at least some of a plurality of images included in each of a plurality of image sets of the same object which have been captured at different imaging dates and times and each of which consists of the plurality of images including at least a plurality of tomographic images acquired by performing tomosynthesis imaging for the object. A setting unit sets at least one past image set, which was acquired at an imaging date and time before the latest imaging date and time and includes images at least some of which have been displayed, among the plurality of image sets as having been displayed.

20 Claims, 13 Drawing Sheets

(56) References Cited

U.S. PATENT DOCUMENTS

2010/0002919 A1    1/2010  Kargar et al.
2015/0356732 A1  12/2015  Fukuda

FOREIGN PATENT DOCUMENTS

| JP | H01-139037 A | 5/1989 |
| JP | 2002-269243 A | 9/2002 |
| JP | 2005-081056 A | 3/2005 |
| JP | 2008-083830 A | 4/2008 |
| JP | 2013-009726 A | 1/2013 |
| JP | 2013-075065 A | 4/2013 |
| JP | 2014-128716 A | 7/2014 |
| JP | 2014-210108 A | 11/2014 |
| JP | 2015-171456 A | 10/2015 |

OTHER PUBLICATIONS

The partial European search report (R. 64 EPC) issued by the European Patent Office dated Jan. 11, 2021, which corresponds to European Patent Application No. 20191411.6-1122 and is related to U.S. Appl. No. 16/938,033.
An Office Action; "Notice of Reasons for Refusal," mailed by the Japanese Patent Office dated Jun. 21, 2022, which corresponds to Japanese Patent Application No. 2019-154276 and is related to U.S. Appl. No. 16/938,033 with English language translation.

\* cited by examiner

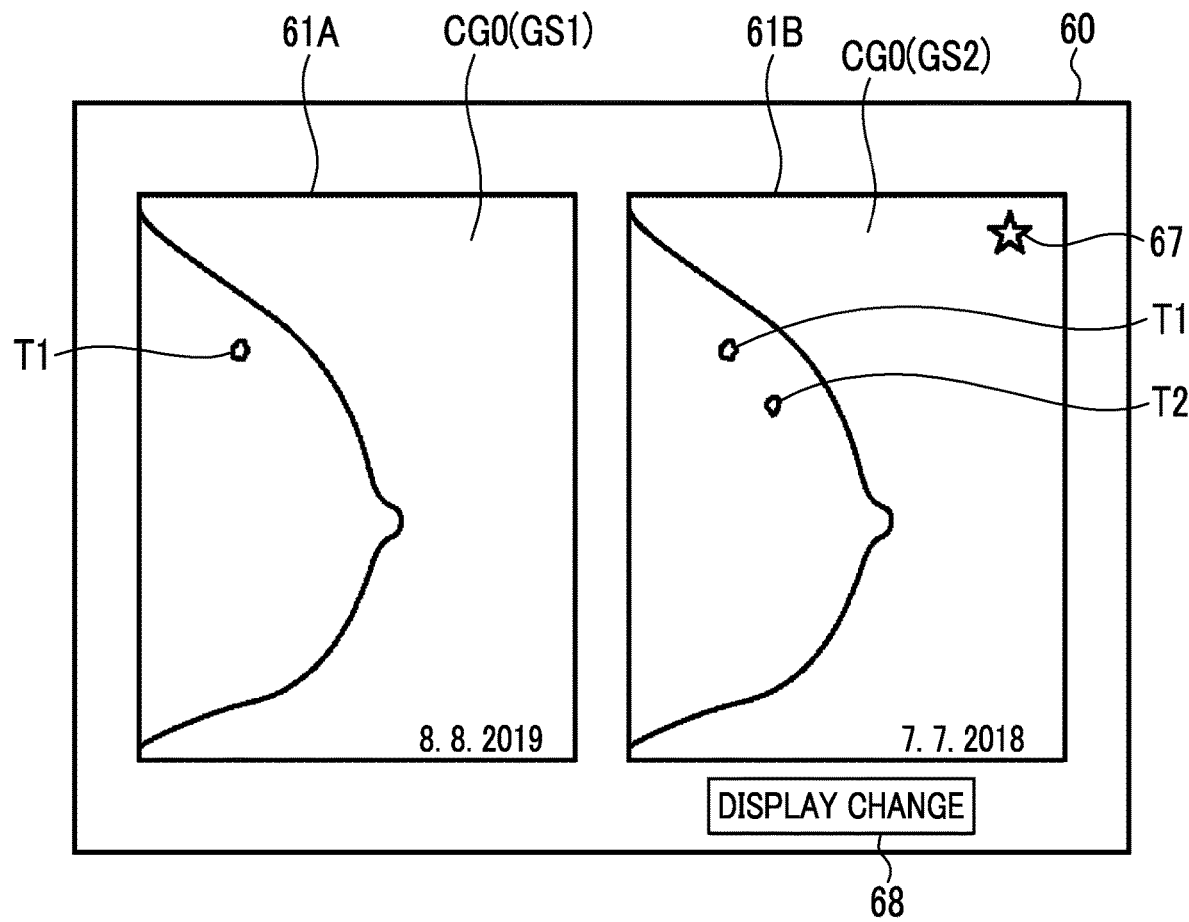

IMAGE DISPLAY DEVICE, IMAGE DISPLAY METHOD, IMAGE DISPLAY PROGRAM, IMAGE MANAGEMENT DEVICE, IMAGE MANAGEMENT METHOD, AND IMAGE MANAGEMENT PROGRAM

CROSS REFERENCE TO RELATED APPLICATIONS

The present application claims priority under 35 U.S.C. § 119 to Japanese Patent Application No. 2019-154276 filed on Aug. 27, 2019. The above application is hereby expressly incorporated by reference, in its entirety, into the present application.

BACKGROUND

Technical Field

The present disclosure relates to an image display device, an image display method, an image display program, an image management device, an image management method, and an image management program that display a plurality of image sets including tomographic images acquired by tomosynthesis imaging for comparative observation over time.

Related Art

In recent years, image diagnosis using a radiography apparatus (called mammography) for capturing an image of the breast has attracted attention in order to promote early detection of breast cancer. Further, in the mammography, tomosynthesis imaging has been proposed which moves a radiation source, irradiates the breast with radiation from a plurality of radiation source positions to acquire a plurality of projection images, adds the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image and imaging is performed for the breast at a plurality of radiation source positions to acquire a plurality of projection images. Then, the projection images are reconstructed using, for example, a back projection method, such as a simple back projection method or a filtered back projection method, or a sequential reconstruction method to generate tomographic images.

The tomographic images are generated in a plurality of tomographic planes of the breast, which makes it possible to separate structures that overlap each other in the depth direction in which the tomographic planes are arranged in the breast. Therefore, it is possible to find an abnormal part such as a lesion that has been difficult to detect in a two-dimensional image (hereinafter, referred to as a simple two-dimensional image) acquired by simple imaging according to the related art.

In addition, a technique has been known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method to generate a pseudo two-dimensional image (hereinafter, referred to as a composite two-dimensional image) corresponding to the simple two-dimensional image (see JP2014-128716A). In the composite two-dimensional image, an abnormal part included in the tomographic image is less affected by the tissues in the thickness direction of the breast than that in the simple two-dimensional image. Therefore, the use of the composite two-dimensional image makes it easy to interpret an abnormal part in the breast with one image.

In contrast, in the medical field, a computer aided diagnosis (hereinafter, referred to as CAD) system has been known which automatically detects an abnormal shadow, such as a lesion, in an image and displays the detected abnormal shadow so as to be highlighted. For example, the CAD is used to detect important structures in diagnosis, such as calcifications, spicula, and tumor, from the tomographic images acquired by the tomosynthesis imaging. In addition, a method has been proposed which, in a case in which a composite two-dimensional image is generated from a plurality of tomographic images acquired by performing the tomosynthesis imaging for the breast, detects a region of interest including an abnormal part using the CAD and combines the detected region of interest on the composite two-dimensional image (see U.S. Pat. No. 8,983,156B).

Further, in some cases, comparative observation over time is performed using the past radiographic images in order to diagnose the healing state or the progress state of a disease. In this case, radiographic images acquired by the latest examination and radiographic images acquired by the past examination are transmitted from a picture archiving and communication system (PACS) that stores a plurality of images for diagnosis to an image interpretation terminal and a radiologist performs comparative image interpretation.

The tomosynthesis imaging is performed to generate a plurality of tomographic images and a composite two-dimensional image. In a case in which the number of types of images used for diagnosis increases, the image storage capacity of the PACS increases. In contrast, the tomosynthesis imaging is performed to generate a large number of images. However, in the actual diagnosis, it may be sufficient to interpret a composite two-dimensional image or one of a plurality of projection images. In addition, it may be sufficient to interpret only the tomographic image in which an abnormal part has been detected by the CAD.

Therefore, a method has been proposed which selects a key tomographic image, such as a tomographic image in which an abnormal part has been detected, from a plurality of tomographic images and stores the selected tomographic image in the PACS. For example, a method has been proposed which receives the designation of a region of interest including an abnormal part in a plurality of tomographic images and stores only a tomographic image including the region of interest in the PACS (see JP2013-075065A). In a case in which only the tomographic image in which an abnormal part is detected by CAD is stored in the PACS, it is possible to reduce the image storage capacity.

In addition, a method has been proposed which records a radiographic image captured in the past on a recording medium for comparative observation over time and deletes a radiographic image captured at the oldest imaging date and time in a case in which the latest radiographic image is recorded on the recording medium (See JP1989-139037A (JP-H01-139037A)). According to the method described in Patent Literature 4, radiographic images of a plurality of imaging dates and times, including a radiographic image of the latest imaging date and time, are recorded on a recording medium.

However, in the method described in JP2013-075065A, the operator needs to set the key image to be stored. Therefore, a burden on the operator is large. Further, the accuracy of the detection result of an abnormal part by the CAD is not always high. Therefore, in a case in which only the tomographic image in which an abnormal part has been detected by the CAD is stored, a situation occurs in which a tomographic image including an abnormal part is not actually stored. In addition, the method described in JP1989-139037A (JP-H01-139037A) deletes the oldest radiographic image among a plurality of radiographic images recorded on the recording medium for comparative observation over time and the capacity of the images stored in the recording medium is not reduced.

SUMMARY OF THE INVENTION

The present disclosure has been made in view of the above-mentioned problems and an object of the present disclosure is to provide a technique that can appropriately reduce the capacity of stored images in a case in which comparative observation over time is performed for images acquired by tomosynthesis imaging.

According to the present disclosure, there is provided an image display device comprising: a display control unit that displays, on a display unit, at least some of a plurality of images included in each of a plurality of image sets of the same object which have been captured at different imaging dates and times and each of which consists of the plurality of images including at least a plurality of tomographic images acquired by performing tomosynthesis imaging for the object; and a setting unit that sets at least one past image set, which was acquired at an imaging date and time before the latest imaging date and time and includes images at least some of which have been displayed, among the plurality of image sets as having been displayed.

The "at least one past image set acquired at the imaging date and time before the latest imaging date and time" includes one or more past image sets acquired at the imaging date and time before the latest imaging date and time and may include all of the past image sets acquired at the imaging date and time before the latest imaging date and time.

The image display device according to the present disclosure may further comprise: a storage unit that stores the plurality of image sets; and a storage control unit that performs a process of reducing a capacity of the past image set that is set as having been displayed on the basis of a setting result of the setting unit.

The "reduction in the capacity of the past image set that is set as having been displayed" includes increasing the compression rate of at least some of the images included in the past image set that is set as having been displayed to be higher than the original compression rate to reduce the capacity and setting the capacity of at least some of the images to zero, that is, deleting the images.

In the image display device according to the present disclosure, in a case in which the past image set that is set as having been displayed includes an image including a detection result of an abnormal part, the storage control unit may reduce a capacity of images other than the image including the detection result of the abnormal part to reduce the capacity of the past image set that is set as having been displayed.

In the image display device according to the present disclosure, in a case in which the past image set that is set as having been displayed includes a composite two-dimensional image generated from a plurality of tomographic images, the storage control unit may reduce a capacity of images other than the composite two-dimensional image to reduce the capacity of the past image set that is set as having been displayed.

The image display device according to the present disclosure may further comprise an abnormal part detection unit that detects an abnormal part from at least some of the images included in the past image set. The storage control unit may reduce a capacity of images other than an image, in which the abnormal part has been detected, among the images included in the past image set that is set as having been displayed to reduce the capacity of the past image set that is set as having been displayed.

The image display device according to the present disclosure may further comprise a combination unit that combines a plurality of tomographic images included in the past image set to generate a composite two-dimensional image. The storage control unit may reduce a capacity of images other than the generated composite two-dimensional image among the images included in the past image set that is set as having been displayed to reduce the capacity of the past image set that is set as having been displayed.

The image display device according to the present disclosure may further comprise: a display control unit that displays, on the display unit, a confirmation screen for allowing an operator to perform a process of reducing the capacity of the past image set that is set as having been displayed on the basis of the setting result of the setting unit; and an input unit that receives a command to reduce the capacity of the past image set that is set as having been displayed from the operator. The storage control unit may reduce the capacity of the past image set that is set as having been displayed on the basis of the command.

The image display device according to the present disclosure may further comprise a communication unit that transmits setting information indicating the setting result of the setting unit to an image management device that stores a plurality of image sets of the same object which have been captured at different imaging dates and times and each of which consists of a plurality of images including at least a plurality of tomographic images acquired by performing the tomosynthesis imaging for the object.

The image display device according to the present disclosure may further comprise a display control unit that displays a confirmation screen for transmitting the setting information to the image management device on the display unit; and an input unit that receives a command to transmit the setting information from the operator. The communication unit may transmit the setting information to the image management device on the basis of the transmission command.

In the image display device according to the present disclosure, the setting unit may receive designation of a past image set to be set as having been displayed and may set the at least one past image set as having been displayed.

In the image display device according to the present disclosure, the object may be a breast.

According to the present disclosure, there is provided an image management device comprising: a storage unit that stores a plurality of image sets of the same object which have been captured at different imaging dates and times and each of which consists of a plurality of images including at least a plurality of tomographic images acquired by performing tomosynthesis imaging for the object; and a storage control unit that performs a process of reducing a capacity of at least one past image set acquired at an imaging date and time before the latest imaging date and time among the plurality of image sets transmitted to an external device.

In the image management device according to the present disclosure, in a case in which the past image set includes an image including a detection result of an abnormal part, the storage control unit may reduce a capacity of images other than the image including the detection result of the abnormal part to reduce the capacity of the past image set.

In the image management device according to the present disclosure, in a case in which the past image set includes a composite two-dimensional image generated from a plurality of tomographic images, the storage control unit may reduce a capacity of images other than the composite two-dimensional image to reduce the capacity of the past image set.

In the image management device according to the present disclosure, in a case in which an image including a detection result of a new abnormal part for the images included in the past image set whose capacity has been reduced is stored in the storage unit, the storage control unit may include the image, in which the new abnormal part has been detected, in the past image set whose capacity has been reduced and may store the image, in which the new abnormal part has been detected, in the storage unit.

In the image management device according to the present disclosure, in a case in which a new composite two-dimensional image for the images included in the past image set whose capacity has been reduced is stored in the storage unit, the storage control unit may include the new composite two-dimensional image in the past image set whose capacity has been reduced and may store the new composite two-dimensional image in the storage unit.

In the image management device according to the present disclosure, the storage control unit may perform a process of reducing a capacity of the past image set on the basis of a setting result of the setting unit in the image display device according to the present disclosure.

According to the present disclosure, there is provided an image display method comprising: displaying, on a display unit, at least some of a plurality of images included in each of a plurality of image sets of the same object which have been captured at different imaging dates and times and each of which consists of the plurality of images including at least a plurality of tomographic images acquired by performing tomosynthesis imaging for the object; and setting at least one past image set, which was acquired at an imaging date and time before the latest imaging date and time and includes images at least some of which have been displayed, among the plurality of image sets as having been displayed.

According to the present disclosure, there is provided an image management method comprising: storing a plurality of image sets of the same object which have been captured at different imaging dates and times and each of which consists of a plurality of images including at least a plurality of tomographic images acquired by performing tomosynthesis imaging for the object; and reducing a capacity of at least one past image set acquired at an imaging date and time before the latest imaging date and time among the plurality of image sets transmitted to an external device.

In addition, programs that cause a computer to perform the image display method and the image management method according to the present disclosure may be provided.

Another image display device according to the present disclosure comprises a memory that stores commands to be executed by a computer and a processor configured to execute the stored commands. The processor performs a process of displaying, on a display unit, at least some of a plurality of images included in each of a plurality of image sets of the same object which have been captured at different imaging dates and times and each of which consists of the plurality of images including at least a plurality of tomographic images acquired by performing tomosynthesis imaging for the object and a process of setting at least one past image set, which was acquired at an imaging date and time before the latest imaging date and time and includes images at least some of which have been displayed, among the plurality of image sets as having been displayed.

Another image management device according to the present disclosure comprises a memory that stores commands to be executed by a computer and a processor configured to execute the stored commands. The processor performs a process of storing a plurality of image sets of the same object which have been captured at different imaging dates and times and each of which consists of a plurality of images including at least a plurality of tomographic images acquired by performing tomosynthesis imaging for the object and a process of reducing a capacity of at least one past image set acquired at an imaging date and time before the latest imaging date and time among the plurality of image sets transmitted to an external device.

According to the present disclosure, in a case in which an image acquired by tomosynthesis imaging is stored for comparative observation over time, it is possible to appropriately reduce the capacity of the stored image.

BRIEF DESCRIPTION OF THE DRAWINGS

FIG. 10 is a diagram illustrating a display screen on which a display change button is displayed.

FIG. 11 is a diagram illustrating setting information.

DETAILED DESCRIPTION

Figure 1:
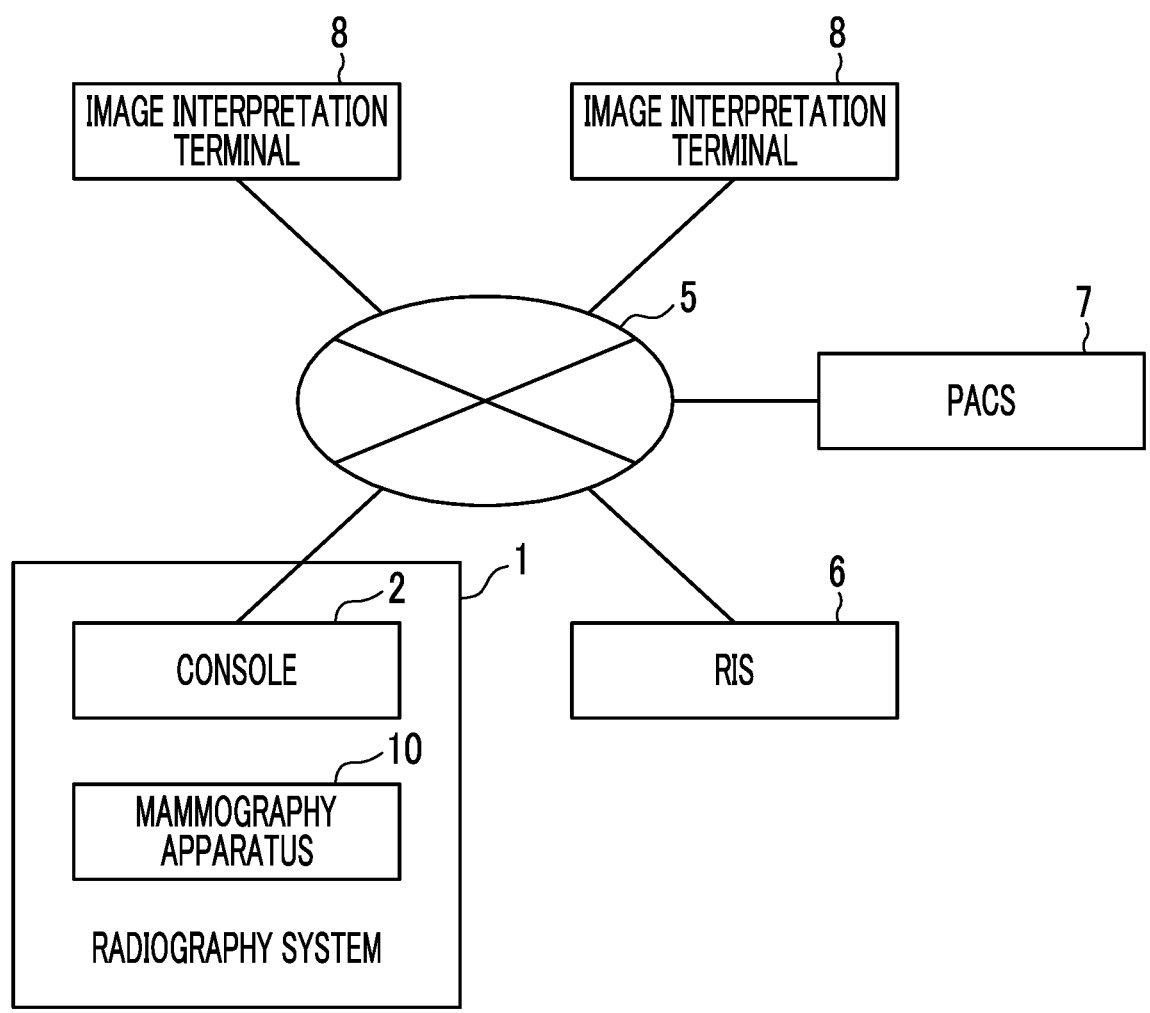
FIG. 1 is a diagram schematically illustrating a configuration of a radiographic image interpretation system to which an image display device and an image management device according to an embodiment of the present disclosure are applied.

Hereinafter, embodiments of the present disclosure will be described with reference to the drawings. FIG. 1 is a diagram schematically illustrating a configuration of a radiographic image interpretation system to which an image display device and an image management device according to an embodiment of the present disclosure are applied. As illustrated in FIG. 1, in the radiographic image interpretation system according to this embodiment, a radiography system 1 including a console 2 and a mammography apparatus 10, a radiology information system (RIS) 6, a picture archiving and communication system (PACS) 7, and a plurality of image interpretation terminals (two image interpretation terminals in FIG. 1) 8 are connected through a network 5 so as to communicate with each other.

Figure 2:
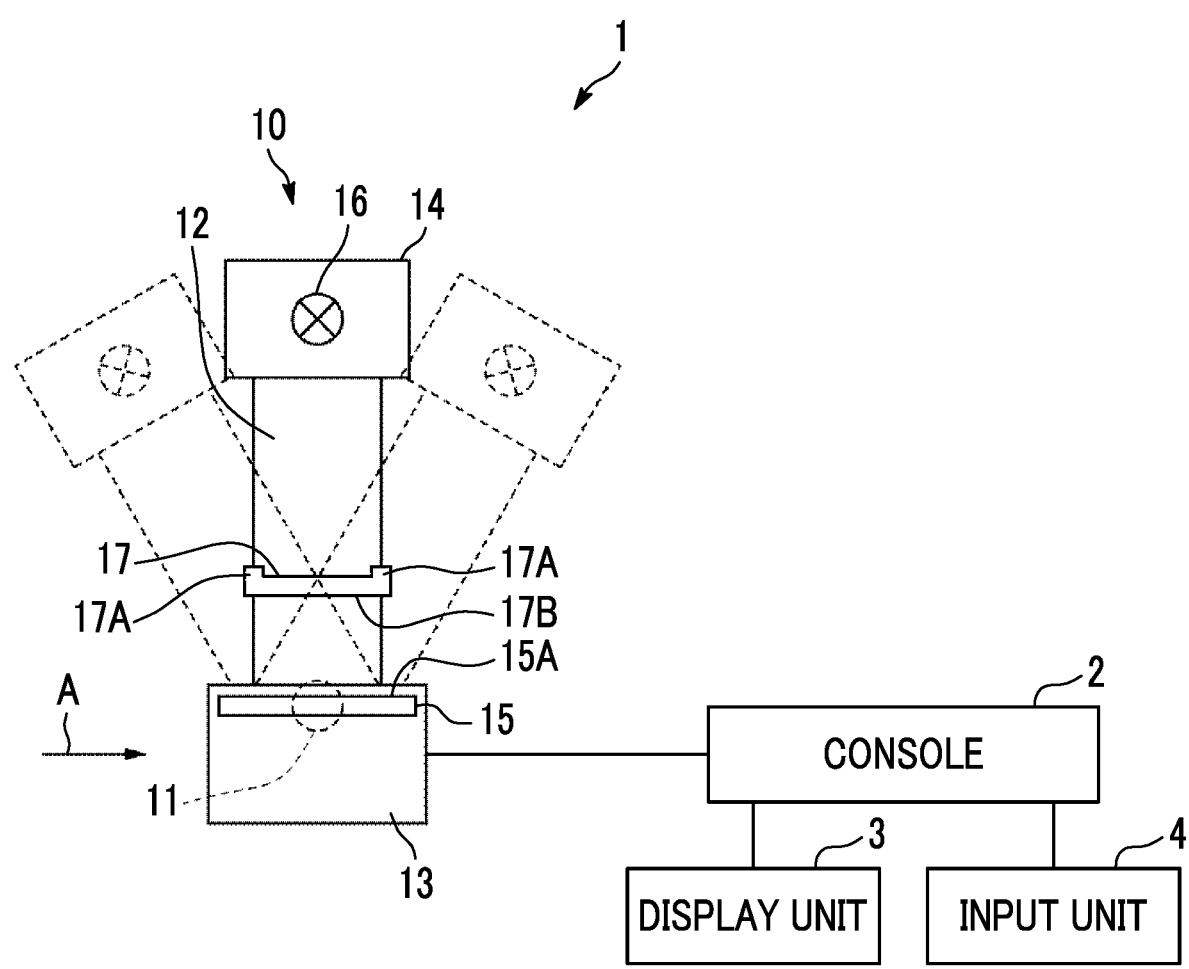
FIG. 2 is a diagram schematically illustrating a configuration of a radiography system.
Figure 3:
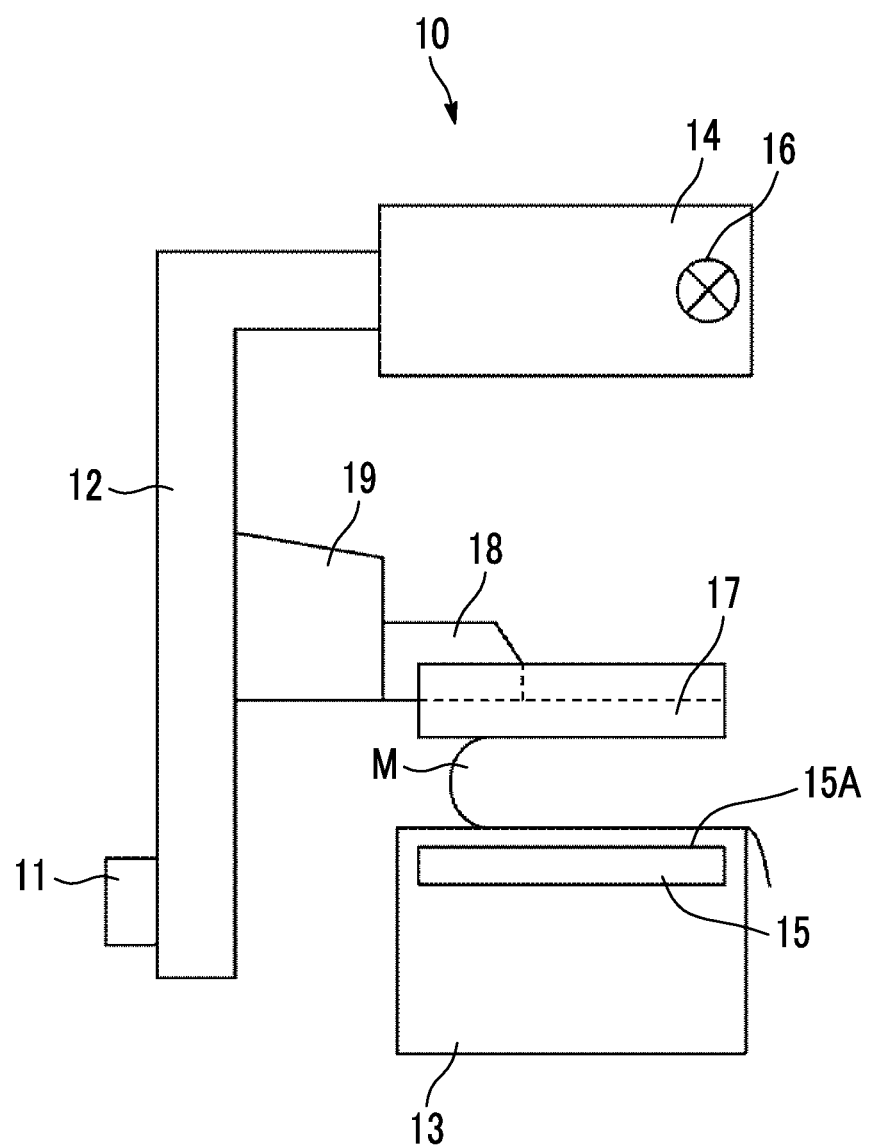
FIG. 3 is a diagram illustrating a mammography apparatus as viewed from a direction of an arrow A in FIG. 2.

FIG. 2 is a diagram schematically illustrating a configuration of the radiography system and FIG. 3 is a diagram illustrating the mammography apparatus included in the radiography system as viewed from the direction of an arrow A in FIG. 2.

As illustrated in FIG. 2, the radiography system 1 includes the console 2 and the mammography apparatus 10. The console 2 comprises a display unit 3 and an input unit 4. The console 2 is connected to the RIS 6 and the PACS 7 through the network 5 so as to communicate therewith.

The radiography system 1 according to this embodiment has a function of capturing the images of a breast M using the mammography apparatus 10 on the basis of a command (imaging order) input from the RIS 6 through the console 2 in response to an operation of an operator, such as a doctor or a radiology technician, and acquiring a tomographic image and a composite two-dimensional image of the breast M. In this embodiment, the mammography apparatus 10 can perform both tomosynthesis imaging and simple imaging in various imaging directions to generate a tomographic image and a two-dimensional breast image of the breast M. The two-dimensional breast image means a breast image acquired by the simple imaging. In this embodiment, the description will be made assuming that the simple imaging is not performed and only the tomosynthesis imaging is performed. An image set including a plurality of tomographic images and a composite two-dimensional image generated in the radiography system 1 as described below is transmitted to the PACS 7 and is then stored therein.

The mammography apparatus 10 comprises an arm portion 12 that is connected to a base (not illustrated) by a rotation shaft 11. An imaging table 13 is attached to one end of the arm portion 12 and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed and only the radiation emitting unit 14 can be rotated. The rotation of the arm portion 12 is controlled by the console 2.

A radiation detector 15, such as a flat panel detector, is provided in the imaging table 13. The radiation detector 15 has a radiation detection surface 15A. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is provided in the imaging table 13.

The radiation detector 15 can repeatedly perform the recording and reading of a radiographic image and may be a so-called direct-type radiation detector that directly converts radiation into charge or a so-called indirect-type radiation detector that converts radiation into visible light once and converts the visible light into a charge signal. As a method for reading a radiographic image signal, it is desirable to use the following method: a so-called thin film transistor (TFT) reading method which turns on and off a TFT switch to read a radiographic image signal; or a so-called optical reading method which emits reading light to read a radiographic image signal. However, the reading method is not limited thereto and other methods may be used.

A radiation source 16 is accommodated in the radiation emitting unit 14. The radiation source 16 emits, for example, X-rays as radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that presses and compresses the breast M, a support portion 18 that supports the compression plate 17, and a movement mechanism 19 that moves the support portion 18 in the vertical direction in FIGS. 2 and 3. An interval between the compression plate 17 and the imaging table 13, that is, a compression thickness is input to the console 2. In addition, the compression plates 17 having a plurality of sizes and shapes corresponding to the types of imaging are prepared. Therefore, the compression plate 17 is attached to the support portion 18 so as to be interchangeable. Further, side walls 17A are formed on the left and right edges of the compression plate 17 in FIG. 2. The side walls 17A are formed in order to reduce the pain of a patient in a case in which the breast M compressed by a compression surface 17B of the compression plate 17 protrudes from the compression plate 17.

The display unit 3 is a display, such as a cathode ray tube (CRT) or a liquid crystal display, and displays messages required for operations in addition to a tomographic image and a composite two-dimensional image which will be described below. The display unit 3 may include a speaker that outputs sound.

The input unit 4 consists of a keyboard, a mouse, or a touch-panel-type input device and receives commands to operate the mammography apparatus 10 from the operator. In addition, the input unit 4 receives the input of various kinds of information required for tomosynthesis imaging, such as imaging conditions, and a command to correct information. In this embodiment, each unit of the mammography apparatus 10 is operated according to the information input by the operator through the input unit 4.

An imaging program for performing, for example, tomosynthesis imaging is installed in the console 2. In this embodiment, the console 2 may be a workstation or a personal computer that is directly operated by the operator or a server computer that is connected to them through a network. The imaging program is stored in a storage device of a server computer connected to the network or a network storage in a state in which it can be accessed from the outside and is downloaded and installed in the computer as required. Alternatively, the imaging program is recorded on a recording medium, such as a digital versatile disc (DVD) or a compact disc read only memory (CD-ROM), is distributed, and is installed in a computer from the recording medium.

Figure 4:
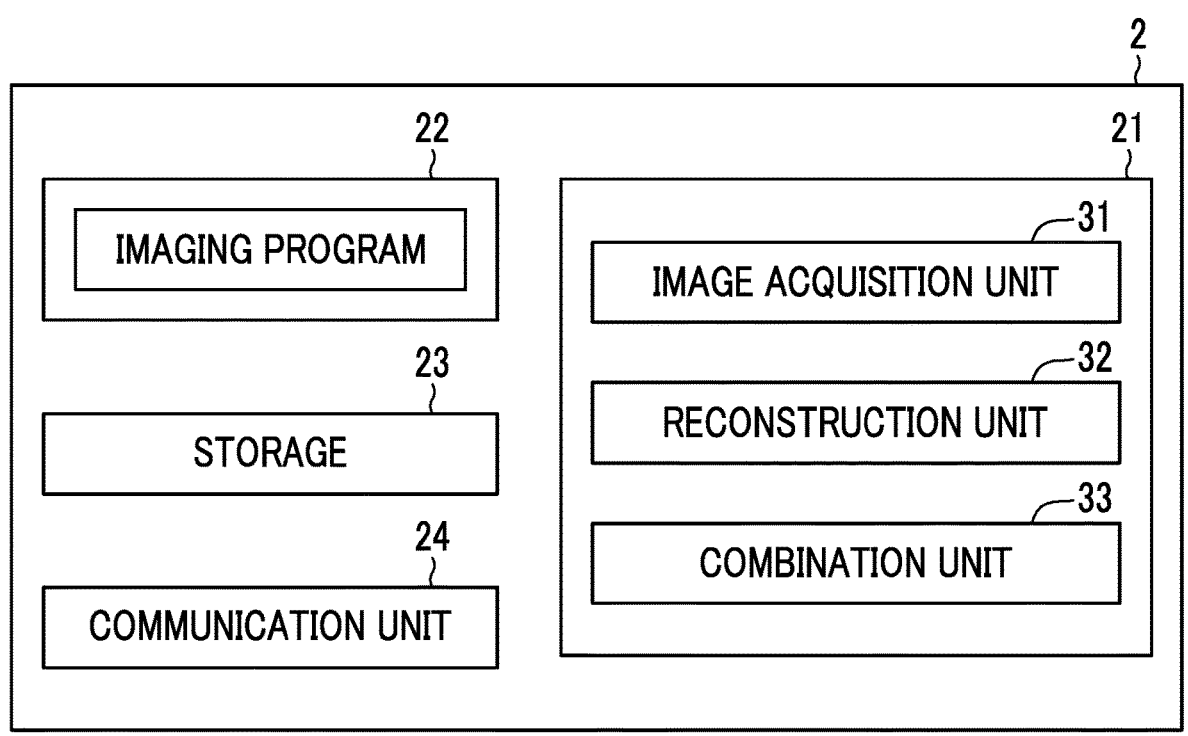
FIG. 4 is a diagram schematically illustrating a configuration of an imaging control device implemented by installing an imaging program in a computer forming a console.

FIG. 4 is a diagram schematically illustrating a configuration of an imaging control device that is implemented by installing the imaging program in a computer forming the console 2. As illustrated in FIG. 4, the imaging control device comprises a central processing unit (CPU) 21, a memory 22, a storage 23, and a communication unit 24 as a standard computer configuration.

The storage 23 is a storage device, such as a hard disk drive or a solid state drive (SSD), and stores various kinds of information including an imaging program for driving each unit of the mammography apparatus 10 to perform tomosynthesis imaging. Further, for example, a projection image acquired by imaging, and tomographic images and a composite two-dimensional image generated as described below are stored in the storage 23.

The communication unit 24 is a network interface that controls the transmission of various kinds of information through the network 5.

The memory 22 temporarily stores, for example, the programs that are stored in the storage 23 in order to cause the CPU 21 to perform various processes. The imaging program defines the following processes as the processes to be performed by the CPU 21: an image acquisition process that causes the mammography apparatus 10 to perform tomosynthesis imaging to acquire a plurality of projection images of the breast M corresponding to each of a plurality of radiation source positions; a reconstruction process that reconstructs the plurality of projection images to generate a plurality of tomographic images in each of a plurality of tomographic planes of the breast M as an object; and a combination process that generates a composite two-dimensional image from the plurality of tomographic images.

The CPU 21 of the console 2 performs these processes according to the imaging program such that the CPU 21 functions as an image acquisition unit 31, a reconstruction unit 32, and a combination unit 33.

Figure 5:
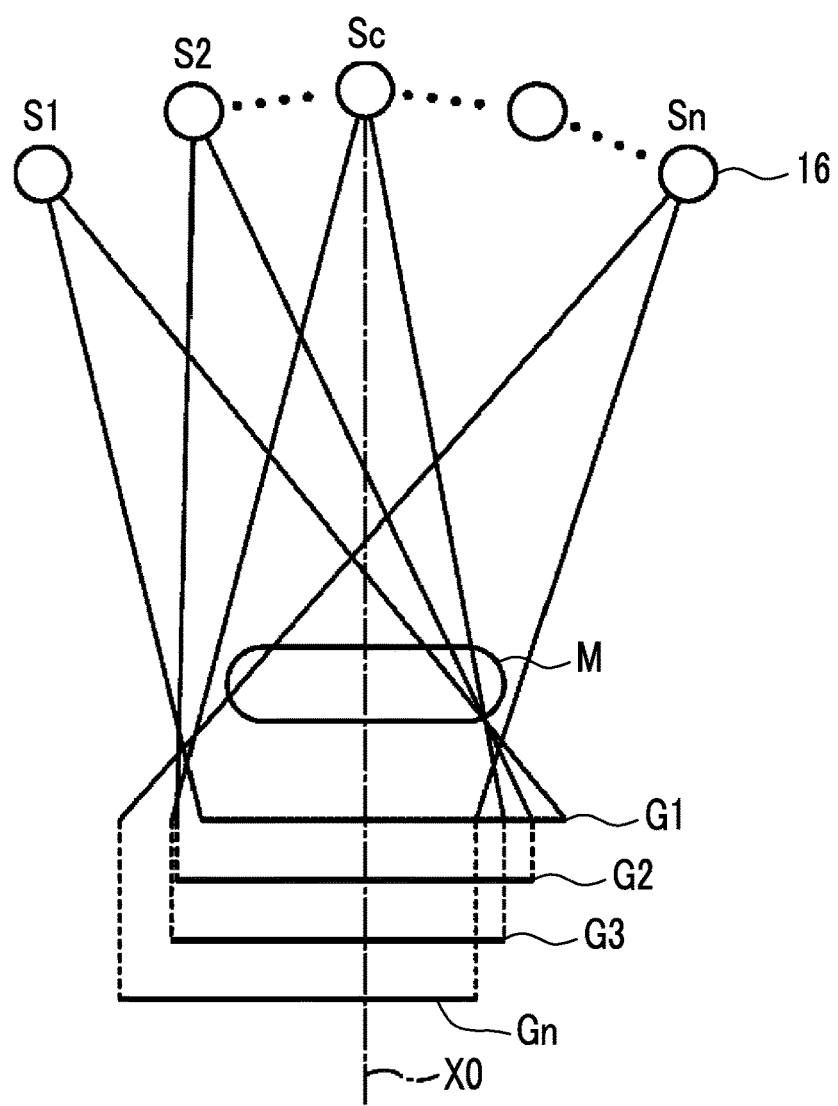
FIG. 5 is a diagram illustrating the acquisition of projection images.

The image acquisition unit 31 rotates the arm portion 12 around the rotation shaft 11 to move the radiation source 16, irradiates the breast M with radiation at a plurality of radiation source positions caused by the movement of the radiation source 16 according to imaging conditions for tomosynthesis imaging, detects the radiation transmitted through the breast M using the radiation detector 15, and acquires a plurality of projection images Gi (i=1 to n, where n is the number of radiation source positions and is, for example, 15) at a plurality of radiation source positions. FIG. 5 is a diagram illustrating the acquisition of the projection images Gi. As illustrated in FIG. 5, the radiation source 16 is moved to each of radiation source positions S1, S2, Sc, . . . , and Sn. The radiation source 16 is driven at each radiation source position to irradiate the breast M with radiation. The radiation detector 15 detects the radiation transmitted through the breast M to acquire projection images G1, G2, Gc, . . . , and Gn corresponding to the radiation source positions S1 to Sn, respectively. Here, the radiation source position Sc illustrated in FIG. 5 is a radiation source position where an optical axis X0 of the radiation emitted from the radiation source 16 is orthogonal to the detection surface 15A of the radiation detector 15. Hereinafter, in some cases, the radiation source position Sc is referred to as a reference radiation source position Sc. At each of the radiation source positions S1 to Sn, the same dose of radiation is emitted to the breast M. The plurality of acquired projection images Gi are stored in the storage 23.

Figure 6:
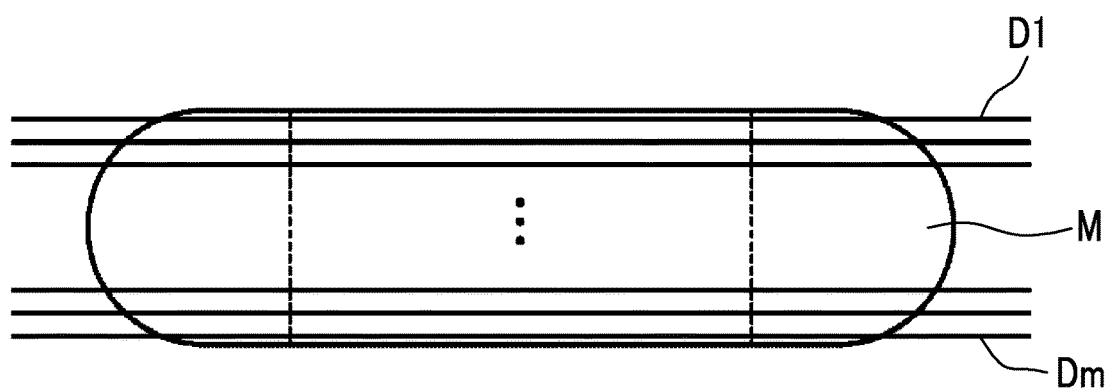
FIG. 6 is a diagram illustrating the generation of tomographic images.

The reconstruction unit 32 reconstructs the projection images Gi to generate the tomographic images in which the desired tomographic planes of the breast M have been highlighted. Specifically, the reconstruction unit 32 reconstructs the plurality of projection images Gi using a known back projection method, such as a simple back projection method or a filtered back projection method, to generate a plurality of tomographic images Dj (j=1 to m) in each of the plurality of tomographic planes of the breast M as illustrated in FIG. 6. In this case, a three-dimensional coordinate position in a three-dimensional space including the breast M is set, pixel values at corresponding pixel positions in the plurality of projection images Gi are reconstructed for the set three-dimensional coordinate position, and pixel values at the coordinate positions are calculated. A three-dimensional image of the breast M is configured by the plurality of tomographic images Dj generated by the reconstruction. Examples of the tomographic images include a slab image having a thickness of, for example, 1 cm.

The combination unit 33 generates a composite two-dimensional image CG0 using the plurality of tomographic images Dj. The composite two-dimensional image CG0 is a pseudo two-dimensional image corresponding to a simple two-dimensional image that is captured by irradiating the breast M with radiation emitted at the reference radiation source position Sc. In this embodiment, the combination unit 33 generates the composite two-dimensional image CG0 using an addition method. The addition method is a method that weights and adds the values of the corresponding pixels in each of the plurality of tomographic images Dj along a viewing direction from the reference radiation source position Sc to the radiation detector 15, that is, the optical axis X0 shown in FIG. 5 in a state in which the tomographic images Dj are stacked. In the addition method, a weight for each pixel during the weighting and addition is set to 1/m in a case in which m is the number of tomographic images Dj. A method for generating the composite two-dimensional image CG0 is not limited to the addition method and a known technique, such as an averaging method, a minimum intensity projection method, or a maximum intensity projection method, can be applied.

The image set including the plurality of tomographic images Dj and the composite two-dimensional image CG0 generated as described above is transmitted to the PACS 7 through the network 5 by the communication unit 24 in response to a command from the input unit 4. In this case, the image set includes identification information (for example, an image ID, a patient name, and an imaging date and time) for uniquely identifying the image set. The image set transmitted to the PACS 7 is stored in the PACS 7. The image set may include at least one of the plurality of projection images Gi.

The image interpretation terminal 8 is a computer that is used by a radiologist who interprets a radiographic image to interpret a radiographic image and to make an interpretation report. The image interpretation terminal 8 includes an image display device according to an embodiment of the present disclosure. Therefore, an image display program according to this embodiment is installed in the image interpretation terminal 8. The image display program is stored in a storage device of a server computer connected to the network or a network storage in a state in which it can be accessed from the outside and is downloaded and installed in the computer as required. Alternatively, the program is recorded on a recording medium, such as a DVD or a CD-ROM, is distributed, and is installed in the computer from the recording medium.

Figure 7:
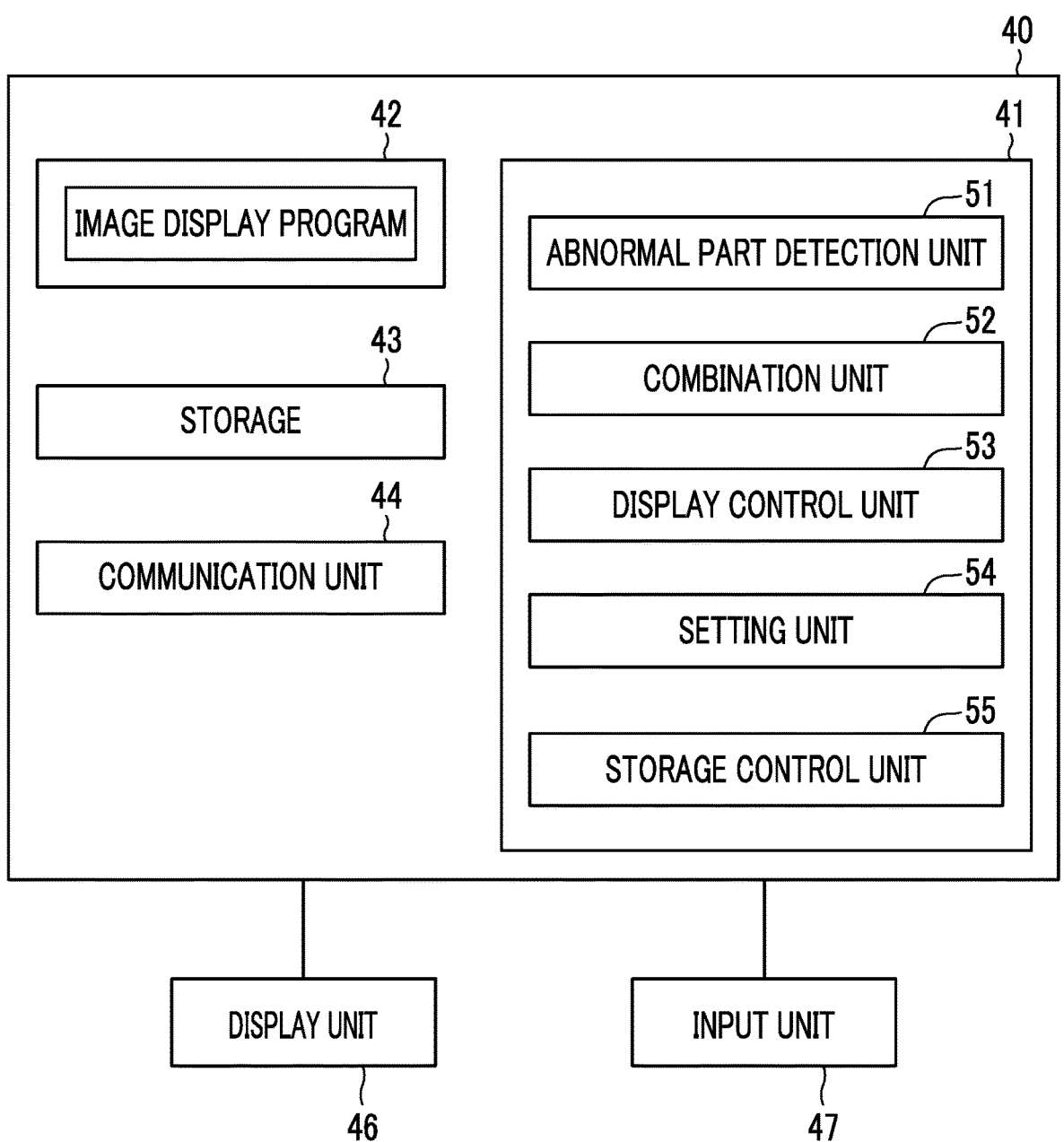
FIG. 7 is a diagram schematically illustrating a configuration of the image display device implemented by installing an image display program in the computer.

FIG. 7 is a diagram schematically illustrating a configuration of the image display device implemented by installing the image display program in the computer. As illustrated in FIG. 7, the image display device 40 comprises a CPU 41, a memory 42, a storage 43, and a communication unit 44 as a standard computer configuration. Further, the image display device 40 is connected to a display unit 46, such as a high-definition liquid crystal display for interpreting a radiographic image, and an input unit 47, such as a keyboard or a mouse.

The storage 43 consists of a storage device, such as a hard disk drive or an SSD, and stores various kinds of information including the image display program according to this embodiment. The storage 43 corresponds to a storage unit.

The memory 42 temporarily stores, for example, the image display program stored in the storage 43 in order to cause the CPU 41 to perform various processes. The image display program defines the following processes as the processes to be executed by the CPU 41: an abnormal part detection process that detects an abnormal part, such as a lesion, from a plurality of tomographic images Dj and composite two-dimensional images CG0 included in a plurality of image sets GSk (k is an integer equal to or greater than 2) which have been captured at different dates and times and have been acquired from the PACS7, as necessary; a combination process that generates a new composite two-dimensional image CG1 from the plurality of tomographic images Dj included in the plurality of image sets GSk as necessary; a display control process that displaying, on the display unit 46, an image for which a display command is given among the plurality of tomographic images Dj and the composite two-dimensional image CG0 included in each of the plurality of image sets GSk for comparative observation over time; a setting process that sets at least one past image set, which was acquired at an imaging date and time before the latest imaging date and time and includes the tomographic images Dj and the composite two-dimensional image CG0 at least some of which have been displayed, among the plurality of image sets GSk as having been displayed; and a storage control process that reduces the capacity of the past image set that is set as having been displayed on the basis of the setting result.

In the following description, it is assumed that, in the plurality of image sets GSk, an image set GS1 includes the images captured at the latest imaging date and time, and the imaging date and time becomes older as k becomes larger.

In a case in which the CPU 41 performs these processes according to the image display program, the CPU 41 functions as an abnormal part detection unit 51, a combination unit 52, a display control unit 53, a setting unit 54, and a storage control unit 55.

The communication unit 44 is a network interface that controls the transmission of various kinds of information through the network 5. In a case in which the identification information of the plurality of acquired image sets is input from the input unit 47, the communication unit 44 transmits the input identification information to the PACS 7 through the network 5. The PACS 7 transmits a plurality of image sets corresponding to the received identification information to the image interpretation terminal 8 through the network 5. Then, the communication unit 44 receives the plurality of image sets and stores them in the storage 43. The communication unit 44 transmits the setting information generated by the setting unit 54 as described below to the PACS 7 through the network 5.

The abnormal part detection unit 51 detects a lesion, such as calcification, as the abnormal part from the plurality of tomographic images Dj and the composite two-dimensional image CG0 included in the image set received by the communication unit 44 as necessary. In this embodiment, the abnormal part is detected from the plurality of tomographic images Dj and the composite two-dimensional image CG0 by a known computer-aided diagnosis (CAD) algorithm. For example, a method described in JP2002-099896A can be used as the CAD algorithm. The method described in JP2002-099896A is a method that detects a calcified region using a shape filter corresponding to a calcified shadow.

The abnormal part detection unit 51 may comprise a discriminator that has been trained to detect an abnormal part by, for example, deep learning and detect the abnormal part from the plurality of tomographic images Dj and the composite two-dimensional image CG0 using the discriminator.

Here, there is a case in which the process of detecting an abnormal part has already been performed for the images included in the image set. In this case, the radiologist may not want to detect the abnormal part again. In contrast, since an algorithm for detecting an abnormal part is improved day by day, the newer algorithm has higher accuracy in detecting the abnormal part. Therefore, even in a case in which the process of detecting an abnormal part has been performed for the images included in the acquired past image set, a new algorithm can be used to detect the abnormal part with higher accuracy. In this case, even though the process of detecting an abnormal part has been performed for the images included in the image set, the radiologist may want to detect the abnormal part again. Therefore, the abnormal part detection unit 51 performs the process of detecting an abnormal part as necessary in response to a command from the radiologist.

The combination unit 52 generates a new composite two-dimensional image CG1 using the plurality of tomographic images Dj included in the plurality of image sets as necessary, similarly to the combination unit 33.

Here, in a case in which the composite two-dimensional image CG0 has already been included in the image set, the radiologist may not want to generate a new composite two-dimensional image CG1. In contrast, since the algorithm for generating a composite two-dimensional image is improved day by day, the newer algorithm generates a higher-quality composite two-dimensional image. Therefore, even in a case in which the composite two-dimensional image CG0 is included in the acquired past image set, a new algorithm can be used to generate a new composite two-dimensional image CG1 with higher quality. In this case, even though the composite two-dimensional image CG0 is included in the image set, the radiologist may want to generate a new composite two-dimensional image CG1. Therefore, the combination unit 52 performs the process of generating a new composite two-dimensional image CG1 as necessary in response to a command from the radiologist.

Figure 8:
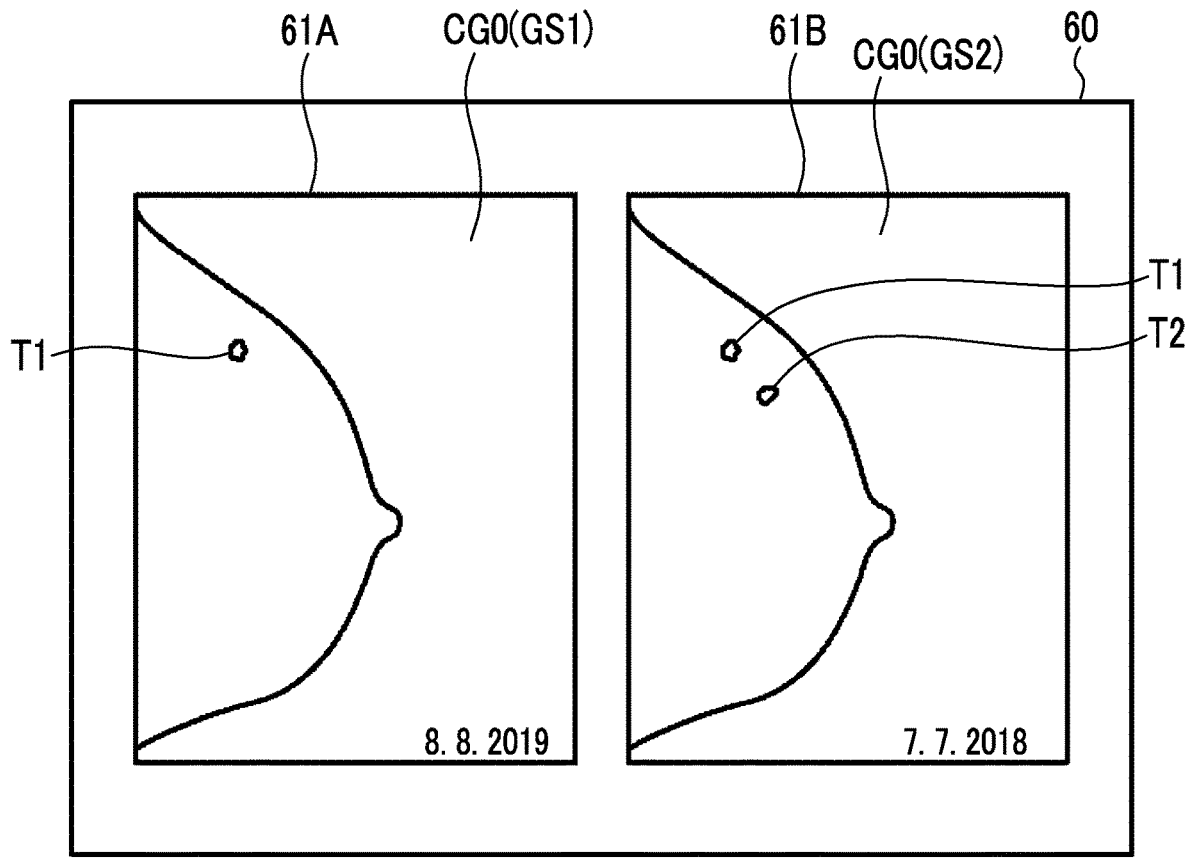
FIG. 8 is a diagram illustrating a display screen for performing comparative observation over time.

The display control unit 53 displays the plurality of image sets on the display unit 46 for comparative observation over time. FIG. 8 is a diagram illustrating a display screen for performing comparative observation over time. As illustrated in FIG. 8, a display screen 60 includes a display region 61A for displaying images included in an image set captured at the latest imaging date and time and a display region 61B for displaying images included in a past image set captured at an imaging date and time before the latest imaging date and time. Then, in a case in which the radiologist who is an operator inputs an image interpretation command to the image interpretation terminal 8, the display control unit 53 displays the composite two-dimensional image CG0 (GS1) included in the image set GS1 captured at the latest imaging date and time in the display region 61A and displays the composite two-dimensional image CG0 (GS2) included in the past image set (for example, GS2) in the display region 61B, as illustrated in FIG. 8. The imaging date and time is displayed so as to be superimposed on each of the composite two-dimensional images CG0 displayed in the display regions 61A and 61B, respectively.

Here, in FIG. 8, two lesions T1 and T2 are included in the composite two-dimensional image CG0 in the past image set GS2. In contrast, only one lesion T1 is included in the composite two-dimensional image CG0 (GS2) in the latest image set GS1. Therefore, the radiologist can compare and interpret two composite two-dimensional images CG0 (GS2) to recognize that the result of treatment is good since the lesion T2 has disappeared.

Instead of displaying the composite two-dimensional image CG0, the tomographic images Dj included in each of the image sets GS1 and GS2 may be displayed. In this case, it is preferable to match the tomographic planes of the tomographic images Dj displayed in each of the display regions 61A and 61B.

In addition, the system may be configured as follows: in a case in which three or more image sets are acquired by the image interpretation terminal 8, an image set to be displayed in the display region 61B can be selected. For example, the system may be configured as follow: in a case in which four image sets GS1 to GS4 are acquired, the radiologist can designate which of the past image sets GS2 to GS4 is displayed in the display region 61B using the input unit 47. Further, all of the past image sets GS2 to GS4 may be displayed side by side in the display region 61B. Furthermore, the past image sets GS2 to GS4 may be displayed in the display region 61B while being sequentially switched. In a case in which the images that are displayed side by side or are displayed while being switched are tomographic images, it is preferable to match the displayed tomographic planes.

The setting unit 54 sets at least one past image set, which was acquired at an imaging date and time before the latest imaging date and time and includes the images at least some of which have been displayed, among the plurality of image sets GSk as having been displayed. In this embodiment, the setting unit 54 sets the past image set as having been displayed by setting a flag indicating that an image has been displayed to the header of at least one of the tomographic image Dj or the composite two-dimensional image CG0 included in the displayed past image set. Specifically, in a case in which two image sets GS1 and GS2 are acquired by the image interpretation terminal 8, the images included in the image set GS2 are certainly displayed for comparative image interpretation. Therefore, the image set GS2 is set as having been displayed. Further, in a case in which four image sets GS1 to GS4 are acquired by the image interpretation terminal 8 and only the image set GS2 is displayed, only the image set GS2 is set as having been displayed.

Figure 9:
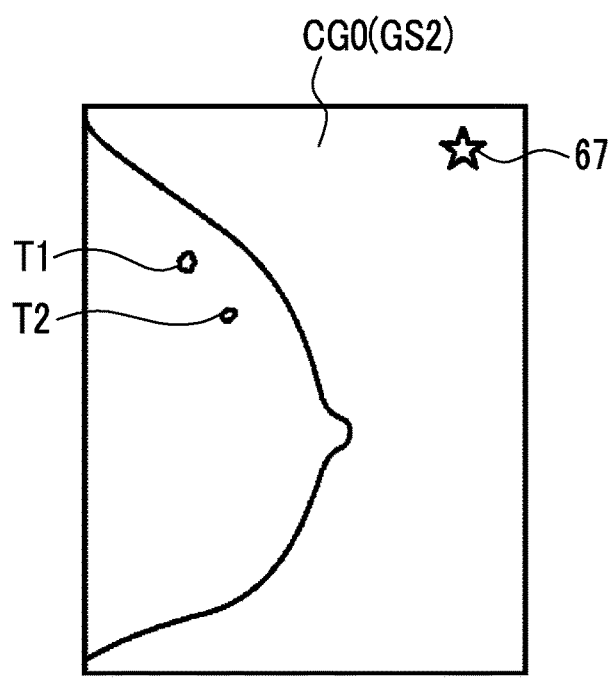
FIG. 9 is a diagram illustrating a state in which a mark is added to a displayed tomographic image.

The setting unit 54 may add a mark indicating that an image has been displayed to the images included in the displayed past image set. FIG. 9 is a diagram illustrating a composite two-dimensional image CG0 (GS2) in the past image set GS2 to which a mark indicating that an image has been displayed is added. As illustrated in FIG. 9, an asterisk mark 67 is added to the composite two-dimensional image CG0 (GS2) in the past image set GS2 that has been displayed.

Further, the setting unit 54 may change the composite two-dimensional image CG0 in the past image set that is set as having been displayed to a non-display state. For example, as illustrated in FIG. 10, a display change button 68 is displayed below the display region 61B. In a case in which the display change button 68 is selected using the input unit 47 during the display of the composite two-dimensional image CG0 in the past image set GS2, the setting of the displayed composite two-dimensional image CG0 may be changed from a "displayed state" to a "non-display state". In a case in which the mark 67 has been added to the composite two-dimensional image CG0 (GS2) as illustrated in FIG. 10 and the display change button 68 is selected, the setting unit 54 deletes the mark 67 from the composite two-dimensional image CG0 (GS2). In a case in which the display change button 68 is selected again, the setting unit 54 may change the setting from the "non-display state" to the "displayed state". In this case, the setting unit 54 may display the mark 67 again.

In a case in which the radiologist completes image interpretation, the radiologist inputs an end command to the image display device 40 through the input unit 47. The setting unit 54 generates setting information for specifying the past image set that is set as having been displayed in response to the end command FIG. 11 illustrates the setting information. As illustrated in FIG. 11, in the setting information 69, a flag indicating whether or not an image has been displayed is set to each of the plurality of image sets GSk (here, four image sets GS1 to GS4). That is, as illustrated in FIG. 11, in the setting information 69, a flag "1" indicating that an image has been displayed is set to the displayed past image sets GS2 and GS3 and a flag "0" is set to the past image set GS4 which has not been displayed.

In addition, the setting information 69 includes the identification information of the image set in which the setting information 69 has been set. Further, in the images included in the image set GS1 captured at the latest imaging date and time, information for specifying the image in which an abnormal part has been detected and abnormal part information indicating, for example, the position and size of the abnormal part detected by the abnormal part detection unit 51 are included in the setting information. In addition, in a case in which the process of detecting an abnormal part has been performed for the images included in the past image set by the abnormal part detection unit 51, information for specifying the image in which an abnormal part has been detected in the past image set and abnormal part information indicating, for example, the position and size of the abnormal part are included in the setting information. Furthermore, in a case in which a new composite two-dimensional image CG1 has been generated from a plurality of tomographic images Dj included in the past image set by the combination unit 52, information indicating the fact is included in the setting information.

In a case in which the setting information 69 is generated, the communication unit 44 transmits the setting information 69 to the PACS 7 through the network 5. In a case in which the abnormal part detection unit 51 has performed the process of detecting an abnormal part for the past image set, the communication unit 44 transmits the image in which an abnormal part has been detected to the PACS 7. In a case in which a new composite two-dimensional image CG1 has been generated for the past image set, the communication unit 44 transmits the new composite two-dimensional image CG1 to the PACS7.

The storage control unit 55 performs a process of reducing the capacity of the past image set that is set as having been displayed among a plurality of image sets stored in the storage 43. Specifically, among the past image sets stored in the storage 43, the past image set that is set as having been displayed is deleted from the storage 43. For example, in a case in which the setting information 69 illustrated in FIG. 11 has been generated, the storage control unit 55 deletes the past image sets GS2 and GS3 set as having been displayed from the storage 43.

Figure 12:
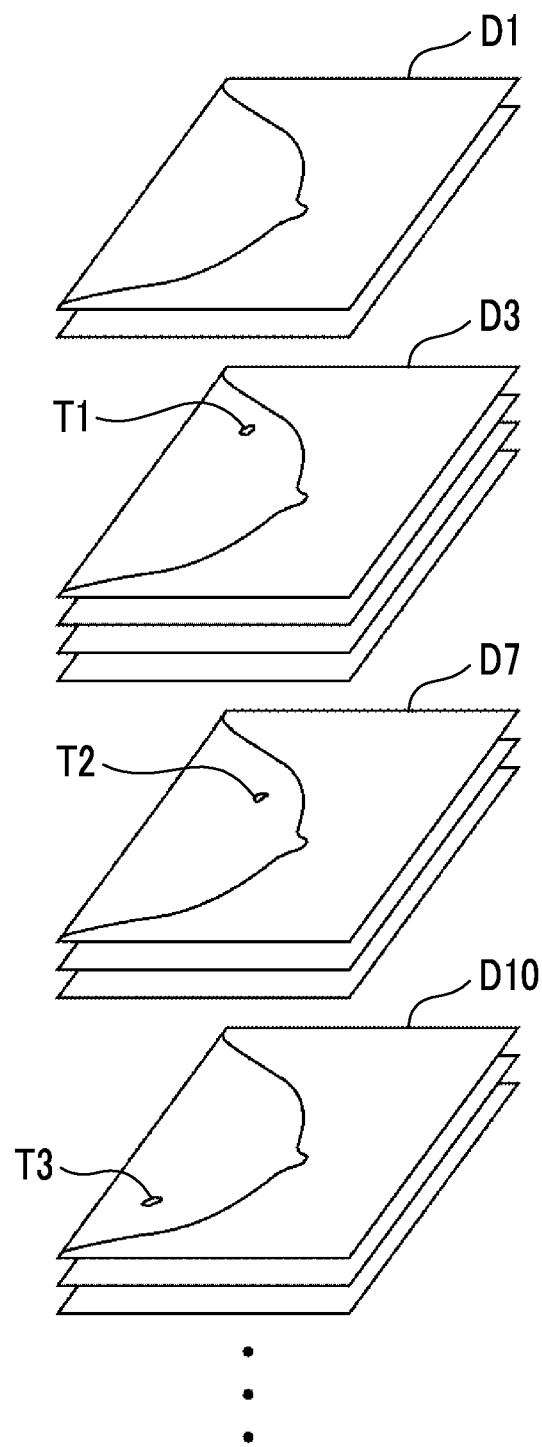
FIG. 12 is a diagram illustrating the deletion of a tomographic image included in a displayed past image set.

In some cases, the detection result of an abnormal part is included in the image included in the past image set that is set as having been displayed. For example, as illustrated in FIG. 12, in some cases, the detection results of the lesions T1 to T3 are included in the tomographic images D3, D7, and D10 among a plurality of tomographic images Dj included in the past image set that is set as having been displayed, respectively. In this case, the storage control unit 55 may delete only tomographic images other than the tomographic images D3, D7, and D10 including the detection results of the lesions. In addition, in a case in which the abnormal part detection unit 51 has detected a new abnormal part in the images included in the past image set that is set as having been displayed, the image in which the new abnormal part has been detected may be stored in the storage 43 and the other images may be deleted.

In a case in which the composite two-dimensional image CG0 is included in the past image set that is set as having been displayed, the storage control unit 55 may leave the composite two-dimensional image CG0 in the storage 43 and may delete only the tomographic images Dj. Further, in a case in which the combination unit 52 has generated a new composite two-dimensional image CG1 from the tomographic images Dj included in the past image set that is set as having been displayed, the new composite two-dimensional image CG1 may be stored in the storage 43 and only the tomographic images Dj may be deleted. In a case in which the composite two-dimensional image CG0 is included in the past image set that is set as having been displayed, a new composite two-dimensional image CG1 may be stored instead of the composite two-dimensional image CG0 or both the composite two-dimensional image CG0 and the new composite two-dimensional image CG1 may be stored.

Figure 13:
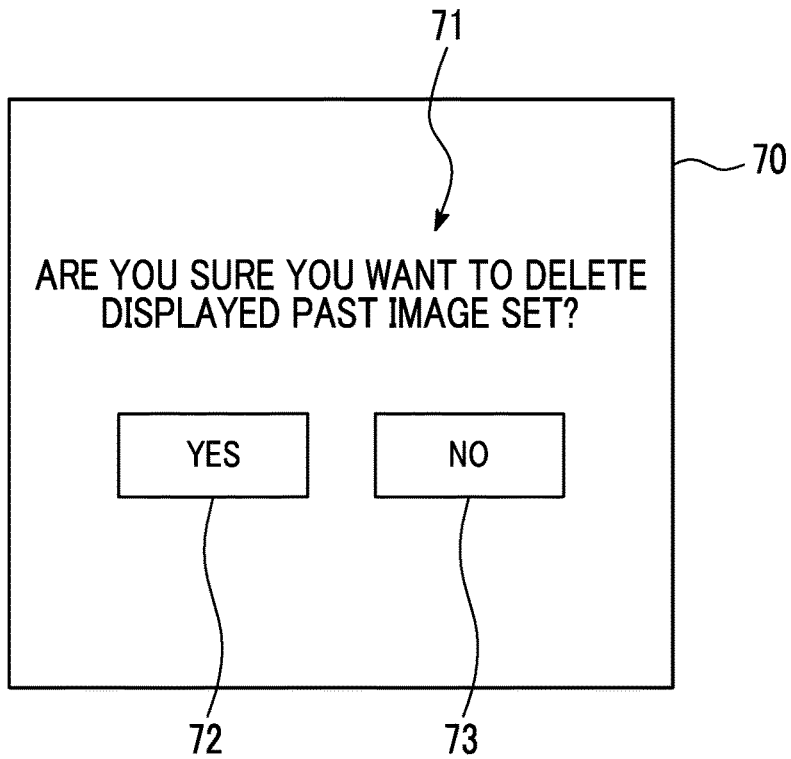
FIG. 13 is a diagram illustrating a confirmation screen for deleting a past image set that is set as having been displayed.

In a case in which the storage control unit 55 deletes the past image set that is set as having been displayed, a deletion confirmation screen may be displayed on the display unit 46. FIG. 13 is a diagram illustrating a confirmation screen for deleting the past image set. As illustrated in FIG. 13, a text 71 of "Are you sure you want to delete the displayed past image set?", a YES button 72, and a NO button 73 are displayed on a confirmation screen 70. In a case in which the radiologist wants to delete the past image set, the radiologist selects the YES button 72 using the input unit 47. Then, the storage control unit 55 deletes the past image set that is set as having been displayed among the image sets stored in the storage 43. In contrast, in a case in which the radiologist selects the NO button 73, the storage control unit 55 does not perform any process. Then, the state in which all of a plurality of past image sets included in the interpreted image sets are stored in the storage 43 is maintained.

Further, instead of deleting the past image set that is set as having been displayed, the storage control unit 55 may increase the compression rate of the images included in the past image set that is set as having been displayed to reduce the capacity of the past image set that is set as having been displayed. For example, the compression rate of the images included in the past image set that is set as having been displayed may be set to be higher than the currently stored compression rate to reduce the capacity of the past image set that is set as having been displayed. In this case, a confirmation screen for asking the radiologist whether or not to increase the compression rate of the images included in the past image set that is set as having been displayed and to store the images may be displayed and the storage control unit 55 may increase the compression rate of the images included in the past image set that is set as having been displayed and store the images in the storage 43 only in a case in which the operator inputs a command to increase the compression rate and to store the images.

In this case, the image including an abnormal part, the image in which an abnormal part has been detected by the abnormal part detection unit 51, the composite two-dimensional image CG0, or the new composite two-dimensional image CG1 may be stored at the original compression rate without increasing the compression rate.

The PACS 7 is a server computer for storing and managing the images transmitted from the radiography system 1. The PACS 7 includes an image management device according to the embodiment of the present disclosure. Therefore, an image management program according to this embodiment is installed in the PACS 7. Hereinafter, only the processes performed by the image management device according to the present disclosure in the PACS 7 will be described and the description of the processes performed by the PACS 7 other than the processes performed by the image management device will be omitted.

Figure 14:
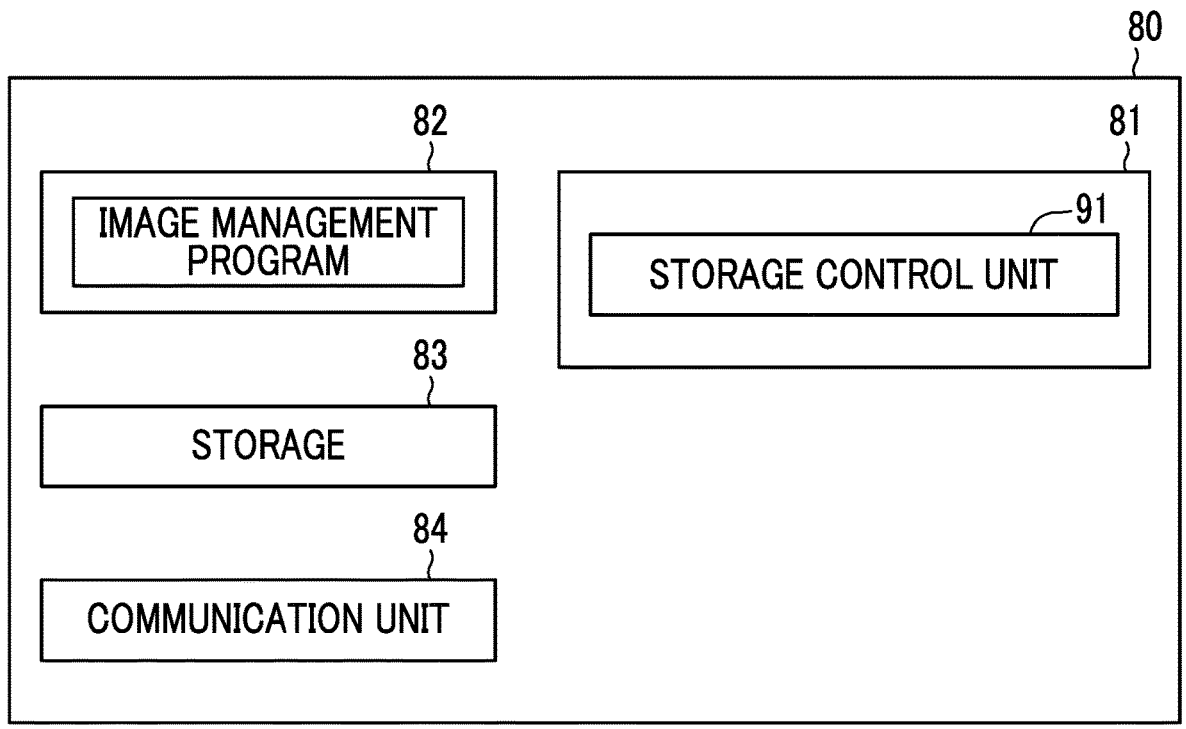
FIG. 14 is a diagram schematically illustrating a configuration of the image management device implemented by installing an image management program in the computer.

FIG. 14 is a diagram schematically illustrating a configuration of an image management device implemented by installing an image management program in a computer. As illustrated in FIG. 14, an image management device 80 comprises a CPU 81, a memory 82, a storage 83, and a communication unit 84 as a standard computer configuration.

The storage 83 consists of a storage device, such as a large-capacity hard disk drive or SSD, and stores various kinds of information including the image management program according to this embodiment in addition to, for example, the received tomographic images. The storage 83 corresponds to a storage unit.

The memory 82 temporarily stores, for example, the image management program stored in the storage 83 in order to cause the CPU 81 to perform various processes. The image management program defines, as the process to be performed by the CPU 81, a storage control process that stores the image set acquired from the radiography system 1 in the storage 83 and reduces the capacity of the past image set that is set as having been displayed on the basis of the setting information 69 transmitted from the image interpretation terminal 8.

Then, the CPU 81 performs the storage control process according to the image management program such that the CPU 81 functions as a storage control unit 91.

Here, the communication unit 84 is a network interface that controls the transmission of various kinds of information through the network 5. The communication unit 84 receives the image set transmitted from the radiography system 1 through the network 5. The image set corresponding to the identification information transmitted from the image interpretation terminal 8 is transmitted to the image interpretation terminal 8 through the network 5. In addition, the communication unit 84 receives, for example, the setting information 69 transmitted by the image interpretation terminal 8.

Further, the storage 83 stores a plurality of image sets GSk of the same object captured at different imaging dates and times.

The storage control unit 91 stores the image set received by the communication unit 84 from the radiography system 1 in the storage 83 so as to be associated with the identification information. Further, the communication unit 84 performs a process of specifying an image set corresponding to the identification information included in the setting information 69 on the basis of the setting information 69 received from the image interpretation terminal 8 and reducing the capacity of the image set. For example, in a case in which the image sets GS1 to GS4 of the same object captured at different imaging dates and times are stored in the storage 83 and the past image sets set as having been displayed by the setting information 69 are the image sets GS2 and GS3, the sets GS2 and GS3 are deleted from the storage 83. Therefore, for the image sets of the same object, the displayed past image sets are deleted from the storage 83.

In some cases, the detection result of an abnormal part is included in the images in the past image set that is set as having been displayed. In this case, similarly to the storage control unit 55 of the image display device 40, the storage control unit 91 may delete only images other than the image including the detection result of the abnormal part. In a case in which the image in which a new abnormal part has been detected by the abnormal part detection unit 51 in the images included in the past image set that is set as having been displayed is transmitted to the PACS 7, the storage control unit 91 may store the image in which the new abnormal part has been detected in the storage 83 and delete the other images from the past image set.

In a case in which the composite two-dimensional image CG0 is included in the past image set that is set as having been displayed, the storage control unit 91 may leave the composite two-dimensional image CG0 and delete only the tomographic images Dj. Further, in a case in which a new composite two-dimensional image CG1 is generated from the tomographic images Dj included in the past image set that is set as having been displayed by the combination unit 52 of the image display device 40 and is transmitted to the PACS 7, the composite two-dimensional image CG1 may be stored in the storage 83 and only the tomographic images Dj may be deleted. In a case in which the composite two-dimensional image CG0 is included in the past image set that is set as having been displayed, a new composite two-dimensional image CG1 may be stored instead of the composite two-dimensional image CG0 or both the composite two-dimensional image CG0 and the new composite two-dimensional image CG1 may be stored.

Instead of deleting the past image set that is set as having been displayed, the storage control unit 91 may increase the compression rate of the images included in the past image set that is set as having been displayed to reduce the capacity of the past image set that is set as having been displayed, similar to the storage control unit 55 of the image display device 40.

Figure 15:
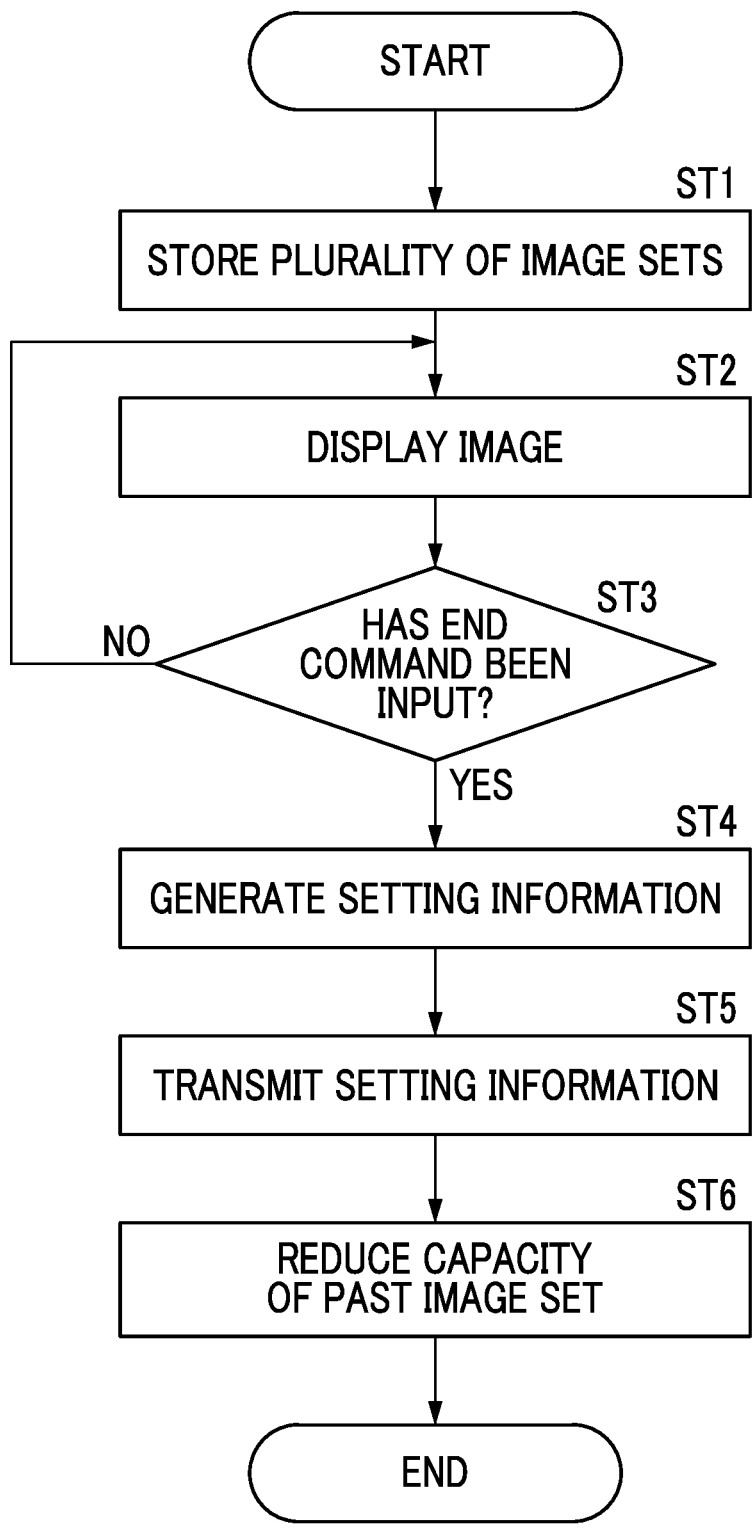
FIG. 15 is a flowchart illustrating a process performed in the image display device according to this embodiment.

Next, a process performed in this embodiment will be described. It is assumed that a plurality of image sets GSk of the same object acquired by the radiography system 1 are stored in the PACS 7 so as to be associated with identification information. First, a process performed by the image display device 40 included in the image interpretation terminal 8 will be described. FIG. 15 is a flowchart illustrating the process performed by the image display device 40. First, a plurality of image sets which have been transmitted from the PACS 7 and is desired to be interpreted are received by the communication unit 24 through the network 5 and are stored in the storage 43 (Step ST1). Then, the display control unit 53 displays the images included in the latest image set GS1 and the images included in the past image set on the display unit 46 for comparative observation over time (Step ST2).

Then, the display control unit 53 determines whether or not an end command has been input from the input unit 47 after the completion of the comparative observation over time (Step ST3). In a case in which the determination result in Step ST3 is "No", the process returns to Step ST2 and Steps ST2 and ST3 are repeated.

In a case in which the determination result in Step ST3 is "Yes", the setting unit 54 sets the past image set including the image displayed on the display unit 46 as having been displayed and generates the setting information 69 (Step ST4). Then, the setting unit 54 transmits the setting information 69 to the PACS 7 through the network 5 using the communication unit 44 (Step ST5). Further, the storage control unit 55 performs a process of deleting the past image set that is set as having been displayed among the plurality of image sets GSk stored in the storage 43 or increasing the compression rate to reduce the capacity of the past image set as having been displayed (Step ST6). Then, the process ends.

Figure 16:
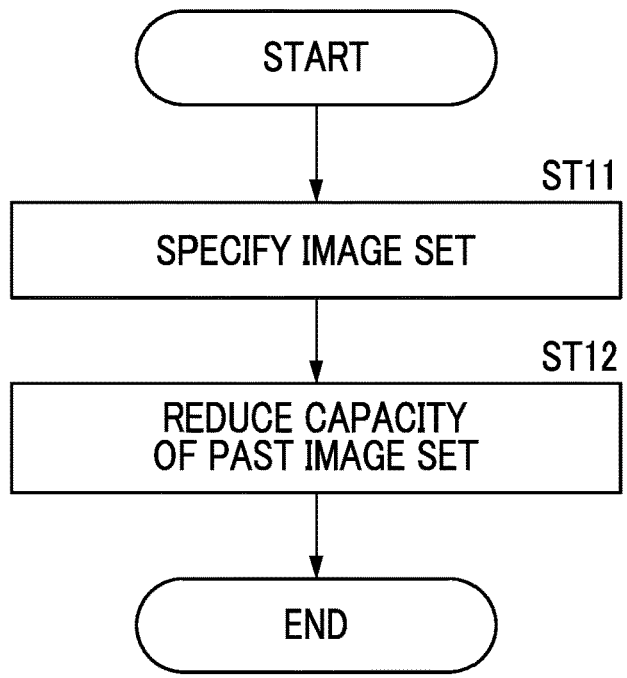
FIG. 16 is a flowchart illustrating a process performed in the image management device according to this embodiment.

FIG. 16 is a flowchart illustrating a process performed by the image management device 80. The process is started by the reception of the setting information 69 transmitted from the image interpretation terminal 8 by the communication unit 84 and the storage control unit 91 specifies the past image set with reference to the identification information of the past image set that is set as having been displayed in the setting information 69 (Step ST11). Then, the storage control unit 91 performs a process of deleting the specified past image set or increasing the compression rate to reduce the capacity of the past image set that is set as having been displayed (Step ST12). Then, the process ends.

As described above, in this embodiment, at least some of a plurality of images included in each of the image sets consisting of the plurality of images including at least a plurality of tomographic images acquired by performing the tomosynthesis imaging for the object are displayed in the image interpretation terminal 8 and at least one past image set acquired at an imaging date and time before the latest imaging date and time among the displayed image sets is set as having been displayed. Therefore, in a case in which a plurality of image sets captured at different imaging dates and times are stored, it is possible to perform a process of reducing the capacity of the past image set that is set as having been displayed. Therefore, according to this embodiment, in a case in which the image acquired by the tomosynthesis imaging is stored for comparative observation over time, it is possible to appropriately reduce the capacity of the stored image.

Figure 17:
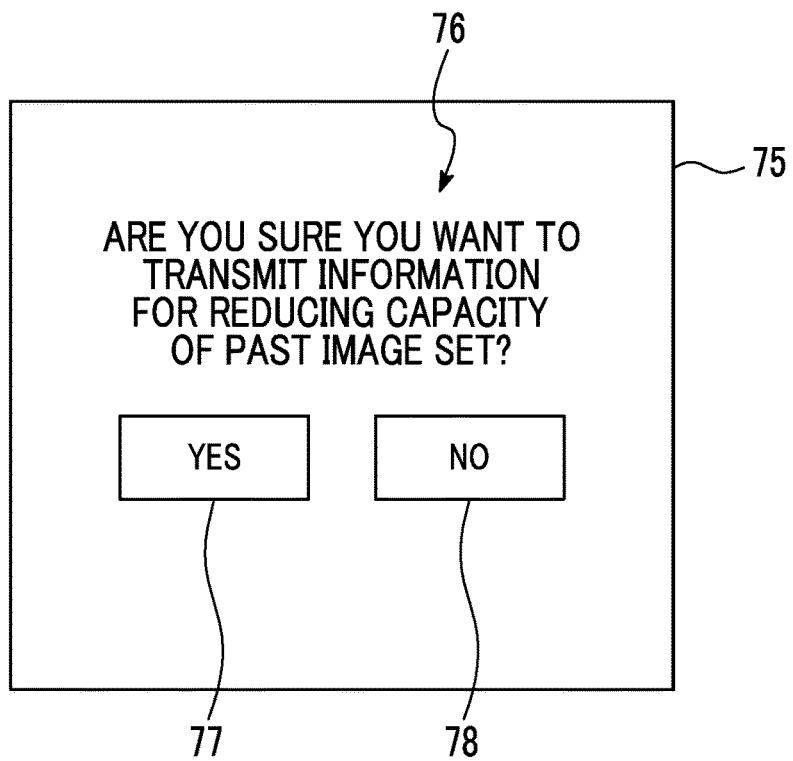
FIG. 17 is a diagram illustrating a confirmation screen for permitting whether or not to transmit the setting information.

In the above-described embodiment, before the setting information 69 is transmitted from the image display device 40 to the PACS 7, a confirmation screen for allowing the radiologist to confirm whether or not to transmit the setting information 69 to the PACS 7 such that the PACS 7 reduces the capacity of the past image set that is set as having been displayed may be displayed on the display unit 46. FIG. 17 is a diagram illustrating a screen for confirming whether or not to permit the transmission of the setting information. As illustrated in FIG. 17, a text 76 of "Are you sure you want to transmit information for reducing the capacity of the past image set?", a YES button 77, and a NO button 78 are displayed on the confirmation screen 75. In a case in which the radiologist wants to reduce the capacity of the past image set that is set as having been displayed in the PACS 7, the radiologist selects the YES button 77 using the input unit 47. Then, the communication unit 44 transmits the setting information 69 to the PACS 7 through the network 5. The PACS 7 performs the process of reducing the capacity of the past image set that is set as having been displayed on the basis of the setting information 69. In contrast, in a case in which the operator selects the NO button 78, the communication unit 44 does not perform any process. As a result, in the PACS 7, a plurality of image sets of the same object are stored without any change.

Figure 18:
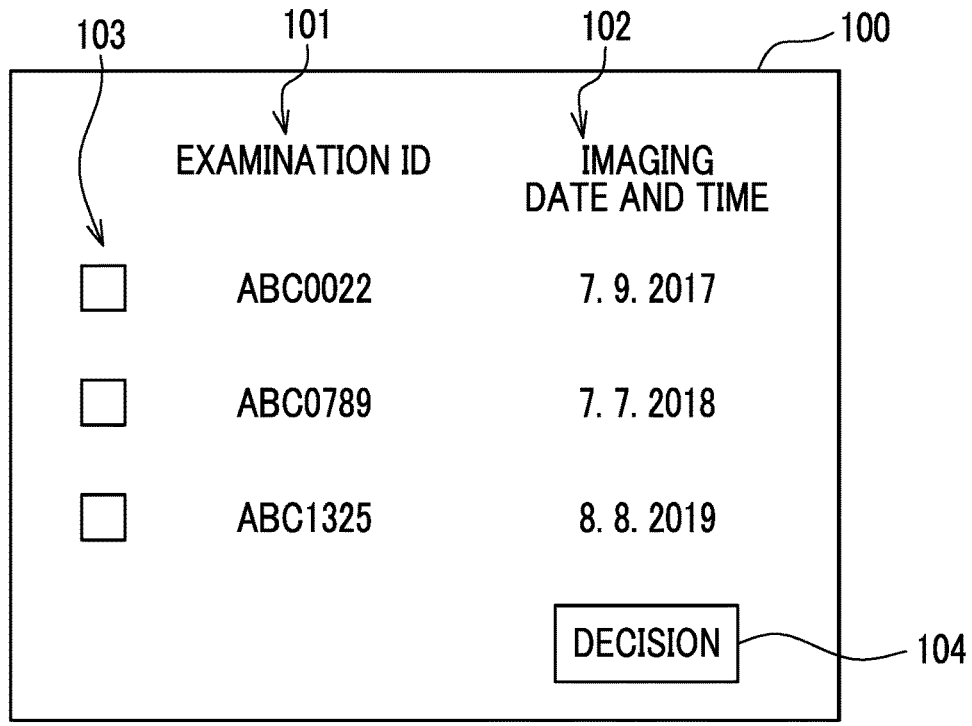
FIG. 18 is a diagram illustrating a past image set selection screen.

Further, in the above-described embodiment, the system may be configured as follows: in a case in which the capacity of a plurality of past image sets is reduced, the radiologist selects which of the past image sets is reduced in capacity. FIG. 18 is a diagram illustrating a past image set selection screen. As illustrated in FIG. 18, an examination ID 101 for specifying a past image set, an imaging date and time 102, a check box 103 for selecting a past image set, and a decision button 104 are displayed on a past image set selection screen 100. The radiologist checks the check box 103 to select a past image set whose capacity is to be reduced among a plurality of past image sets displayed on the selection screen 100. Then, in a case in which the radiologist selects the decision button 104, the image display device 40 of the image interpretation terminal 8 performs a process of reducing the capacity of the selected past image set. In this case, the setting information 69 includes information for specifying the selected past image set. The image management device 80 of the PACS 7 performs a process of reducing the capacity of the past image set included in the setting information 69.

In the above-described embodiment, the image management device 80 of the PACS 7 performs the process of reducing the capacity of the past image set stored in the storage 83 on the basis of the setting information 69 transmitted from the image display device 40 of the image interpretation terminal 8. However, the present disclosure is not limited thereto. In a case in which a plurality of image sets are transmitted from the PACS 7 to the image interpretation terminal 8, the image management device 80 may perform the process of reducing the capacity of the past image set captured at the imaging date and time before the latest imaging date and time among the plurality of transmitted image sets. Hereinafter, this will be described as another embodiment performed by the image management device.

Figure 19:
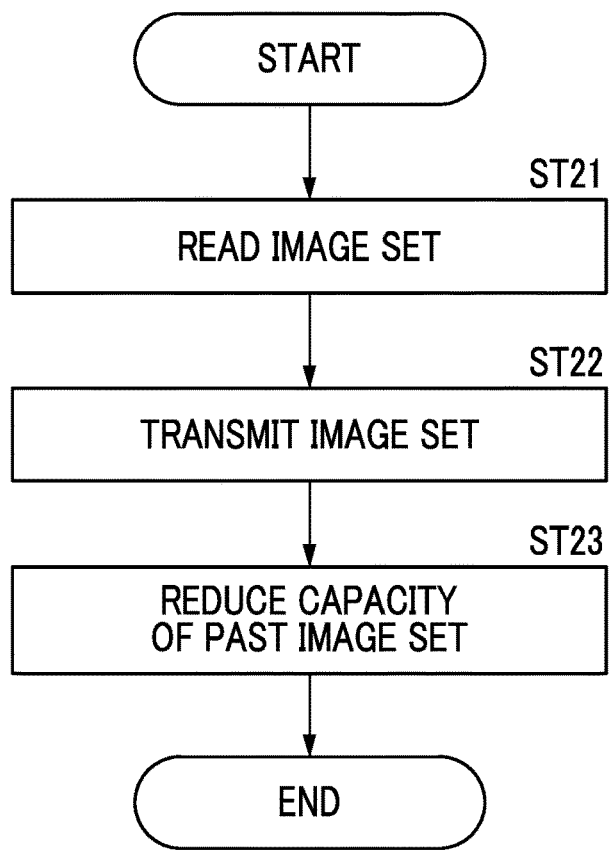
FIG. 19 is a flowchart illustrating a process performed in an image management device according to another embodiment.

FIG. 19 is a flowchart illustrating a process performed by the image management device 80 according to another embodiment. The process is started by the reception of the identification information of a plurality of image sets transmitted to the image interpretation terminal 8 by the communication unit 84 and the storage control unit 91 reads a plurality of image sets corresponding to the received identification information from the storage 83 (Step ST21). The communication unit 84 transmits the plurality of image sets to the image interpretation terminal 8 (Step ST22). Then, the storage control unit 91 performs a process of deleting the past image set captured at the imaging date and time before the latest imaging date and time among the plurality of image sets transmitted to the image interpretation terminal 8 or increasing the compression rate to reduce the capacity of the past image set that is set as having been displayed (Step ST23). Then, the process ends.

In another embodiment, in a case in which the detection result of the abnormal part is included in the image included in the past image set transmitted to the image interpretation terminal 8, the storage control unit 91 may delete only images other than the image including the detection result of the abnormal part or may increase the compression rate, similarly to the storage control unit 55 of the image display device 40. Further, in some cases, in the images included in the past image set, an abnormal part is newly detected by the abnormal part detection unit 51 of the image display device 40 in the image interpretation terminal 8 and the image in which the abnormal part has been detected is transmitted to the PACS 7. In this case, the storage control unit 91 may include the image, in which the abnormal part has been newly detected, in the past image set which corresponds to the image and whose capacity has been reduced and store the past image set in the storage 83.

In a case in which the composite two-dimensional image CG0 is included in the past image set transmitted to the image interpretation terminal 8, the storage control unit 91 may leave the composite two-dimensional image CG0 and delete only the tomographic images Dj or increases the compression rate. Further, in some cases, the combination unit 52 of the image display device 40 generates a new composite two-dimensional image CG1 from the tomographic images Dj included in the past image set and transmits the new composite two-dimensional image CG1 to the PACS 7. In this case, the new composite two-dimensional image CG1 may be included in the corresponding past image set whose capacity has been reduced and may be stored in the storage 83 to delete only the tomographic images Dj or to increase the compression rate. In a case in which the composite two-dimensional image CG0 is included in the past image set whose capacity has been reduced, a new composite two-dimensional image CG1 may be stored instead of the composite two-dimensional image CG0 or both the composite two-dimensional image CG0 and the new composite two-dimensional image CG1 may be stored.

In the above-described embodiment, a plurality of received image sets are stored in the image interpretation terminal 8. However, the plurality of received image sets may not be stored in the storage 43 in the image interpretation terminal 8.

Further, in the above-described embodiment, in the image display device 40 of the image interpretation terminal 8, the abnormal part detection unit 51 detects an abnormal part, such as a lesion, from the tomographic images Dj using the CAD. However, the present disclosure is not limited thereto. In addition, the following configuration may be used: the tomographic images Dj are displayed on the display unit 46 and the radiologist selects an abnormal part included in the tomographic images Dj using the input unit 47.

Further, the radiation in the above-described embodiment is not particularly limited. For example, α-rays or γ-rays can be applied in addition to the X-rays.

Further, in the above-described embodiment, for example, the following various processors can be used as the hardware structure of processing units performing various processes, such as the abnormal part detection unit 51, the combination unit 52, the display control unit 53, the setting unit, 54, and the storage control unit 55 of the image display device 40, and the storage control unit 91 of the image management device 80. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An image display device comprising at least one processor, wherein the processor is configured to:
   display, on a display, at least some of a plurality of images included in each of a plurality of image sets of the same object which have been captured at different imaging dates and times and each of which consists of a plurality of images including at least a plurality of tomographic images acquired by performing tomosynthesis imaging for the object; and
   set at least one past image set, which was acquired at an imaging date and time before the latest imaging date and time and includes images at least some of which have been displayed, among the plurality of image sets as having been displayed, wherein
   a storage stores the plurality of image sets, and
   the processor is configured to perform a process of reducing a capacity of the past image set, that is set as having been displayed by the processor, in order to reduce the image storage capacity of the storage.

2. The image display device according to claim 1, wherein,
   in a case in which the past image set that is set as having been displayed includes an image including a detection result of an abnormal part, the processor is configured to reduce a capacity of images other than the image including the detection result of the abnormal part to reduce the capacity of the past image set that is set as having been displayed.

3. The image display device according to claim 1, wherein,
   in a case in which the past image set that is set as having been displayed includes a composite two-dimensional image generated from a plurality of tomographic images, the processor is configured to reduce a capacity of images other than the composite two-dimensional image to reduce the capacity of the past image set that is set as having been displayed.

4. The image display device according to claim 1, wherein the processor is configured to:
   detect an abnormal part from at least some of the images included in the past image set; and
   reduce a capacity of images other than an image, in which the abnormal part has been detected, among the images included in the past image set that is set as having been displayed to reduce the capacity of the past image set that is set as having been displayed.

5. The image display device according to claim 1, wherein the processor is configured to:
   combine a plurality of tomographic images included in the past image set to generate a composite two-dimensional image; and
   reduce a capacity of images other than the generated composite two-dimensional image among the images included in the past image set that is set as having been displayed to reduce the capacity of the past image set that is set as having been displayed.

6. The image display device according to claim 1, wherein the processor is configured to:
   display, on the display, a confirmation screen for allowing an operator to perform a process of reducing the capacity of the past image set that is set as having been displayed by the processor;
   receive a command to reduce the capacity of the past image set that is set as having been displayed from the operator; and
   reduce the capacity of the past image set that is set as having been displayed on the basis of the command.

7. The image display device according to claim 1, wherein the processor is configured to:
   transmit setting information to an image management device that stores a plurality of image sets of the same object which have been captured at different imaging dates and times and each of which consists of a plurality of images including at least a plurality of tomographic images acquired by performing the tomosynthesis imaging for the object, and
   the setting information indicates that an image set that has been displayed is set as having been displayed by the processor.

8. The image display device according to claim 7, wherein the processor is configured to:
   display a confirmation screen for transmitting the setting information to the image management device on the display;
   receive a command to transmit the setting information from the operator; and
   transmit the setting information to the image management device on the basis of the transmission command.

9. The image display device according to claim 1, wherein processor is configured to receive designation of a past image set to be set as having been displayed and sets the at least one past image set as having been displayed.

10. The image display device according to claim 1, wherein
    the object is a breast.

11. An image management device comprising:
at least one processor; and
a storage that stores a plurality of image sets of the same object which have been captured at different imaging dates and times and each of which consists of a plurality of images including at least a plurality of tomographic images acquired by performing tomosynthesis imaging for the object; wherein
the processor is configured to perform a process of reducing a capacity of at least one past image set acquired at an imaging date and time before the latest imaging date and time among the plurality of image sets transmitted to an external device in order to reduce the image storage capacity of the storage.

12. The image management device according to claim 11, wherein,
in a case in which the past image set includes an image including a detection result of an abnormal part, the processor is configured to reduce a capacity of images other than the image including the detection result of the abnormal part to reduce the capacity of the past image set.

13. The image management device according to claim 11, wherein,
in a case in which the past image set includes a composite two-dimensional image generated from a plurality of tomographic images, the processor is configured to reduce a capacity of images other than the composite two-dimensional image to reduce the capacity of the past image set.

14. The image management device according to claim 11, wherein,
in a case in which an image including a detection result of a new abnormal part for the images included in the past image set whose capacity has been reduced is stored in the storage, the processor is configured to include the image, in which the new abnormal part has been detected, in the past image set whose capacity has been reduced and stores the image, in which the new abnormal part has been detected, in the storage.

15. The image management device according to claim 11, wherein,
in a case in which a new composite two-dimensional image for the images included in the past image set whose capacity has been reduced is stored in the storage, the processor is configured to include the new composite two-dimensional image in the past image set whose capacity has been reduced and stores the new composite two-dimensional image in the storage.

16. The image management device according to claim 11, wherein
the processor is configured to perform a process of reducing a capacity of the past image set that is set as having been displayed by the image display device according to claim 1.

17. An image display method comprising:
displaying, on a display, at least some of a plurality of images included in each of a plurality of image sets of the same object which have been captured at different imaging dates and times and each of which consists of the plurality of images including at least a plurality of tomographic images acquired by performing tomosynthesis imaging for the object;
setting at least one past image set, which was acquired at an imaging date and time before the latest imaging date and time and includes images at least some of which have been displayed, among the plurality of image sets as having been displayed; and
performing a process of reducing a capacity of the past image set that is set as having been displayed in order to reduce the image storage capacity of a storage that stores the plurality of image sets.

18. An image management method comprising:
storing a plurality of image sets of the same object which have been captured at different imaging dates and times and each of which consists of a plurality of images including at least a plurality of tomographic images acquired by performing tomosynthesis imaging for the object; and
reducing a capacity of at least one past image set acquired at an imaging date and time before the latest imaging date and time among the plurality of image sets transmitted to an external device in order to reduce the image storage capacity of a storage that stores the plurality of image sets.

19. A non-transitory computer-readable storage medium that stores an image display program that causes a computer to perform:
displaying, on a display, at least some of a plurality of images included in each of a plurality of image sets of the same object which have been captured at different imaging dates and times and each of which consists of the plurality of images including at least a plurality of tomographic images acquired by performing tomosynthesis imaging for the object;
setting at least one past image set, which was acquired at an imaging date and time before the latest imaging date and time and includes images at least some of which have been displayed, among the plurality of image sets as having been displayed; and
performing a process of reducing a capacity of the past image set, that is set as having been displayed, in order to reduce the image storage capacity of a storage that stores the plurality of image sets.

20. A non-transitory computer-readable storage medium that stores an image display program that causes a computer to perform:
storing a plurality of image sets of the same object which have been captured at different imaging dates and times and each of which consists of a plurality of images including at least a plurality of tomographic images acquired by performing tomosynthesis imaging for the object; and
performing a process of reducing a capacity of at least one past image set acquired at an imaging date and time before the latest imaging date and time among the plurality of image sets transmitted to an external device in order to reduce the image storage capacity of a storage that stores the plurality of image sets.

* * * * *